United States Patent
Niu et al.

(10) Patent No.: US 10,815,486 B2
(45) Date of Patent: Oct. 27, 2020

(54) CHEMICALLY MODIFIED AMPA RECEPTOR RNA APTAMERS

(71) Applicant: The Research Foundation for the State University of New York, Albany, NY (US)

(72) Inventors: Li Niu, Loudonville, NY (US); Zhen Huang, Great Falls, VA (US)

(73) Assignee: THE RESEARCH FOUNDATION FOR THE STATE UNIVERSITY OF NEW YORK, Albany, NY (US)

(*) Notice: Subject to any disclaimer, the term of this patent is extended or adjusted under 35 U.S.C. 154(b) by 17 days.

(21) Appl. No.: 16/028,067

(22) Filed: Jul. 5, 2018

(65) Prior Publication Data

US 2019/0010498 A1 Jan. 10, 2019

Related U.S. Application Data

(60) Provisional application No. 62/528,763, filed on Jul. 5, 2017.

(51) Int. Cl.
  *C12N 15/115* (2010.01)
  *A61P 25/28* (2006.01)
  *A61P 29/02* (2006.01)

(52) U.S. Cl.
  CPC ............ *C12N 15/115* (2013.01); *A61P 25/28* (2018.01); *A61P 29/02* (2018.01); *C12N 2310/16* (2013.01); *C12N 2310/322* (2013.01)

(58) Field of Classification Search
  CPC ........ A61P 25/28; A61P 29/02; C12N 15/115; C12N 2310/16; C12N 2310/322; C12N 2310/3533

USPC ............... 435/6.1, 91.1, 91.31, 455, 458; 514/44 A; 536/23.1, 24.5
See application file for complete search history.

(56) References Cited

U.S. PATENT DOCUMENTS 5,849,546 A 12/1998 Sousa et al.
2008/0138408 A1 6/2008 Venkatesh et al.

FOREIGN PATENT DOCUMENTS

EP 1907590 B1 9/2012
WO 0109157 A1 2/2001

OTHER PUBLICATIONS

Cook et al., "TDP-43 in Neurodegenerative Disorders," Expert Opin. Biol. Ther. 8(7):969-78 (2008).
Huang et al., "Chemically Modified, α-Amino-3-Hydroxy-5-Methyl-4-Isoxazole (AMPA) Receptor RNA Aptamers Designed for in Vivo Use," ACS Chem. Neurosci. 8:2437-45 (2017).

*Primary Examiner* — Jane J Zara
(74) *Attorney, Agent, or Firm* — Michael Krenicky; Garrett Smith; Steven Wood

(57) ABSTRACT

Disclosed is an RNA aptamer, a synthetic oligonucleotide of 2'-fluoro-modified A, U, and C nucleotides, with improved stability compared to its unmodified counterpart. Like the unmodified aptamer, however, the modified version is a potent glutamate receptor antagonist. Additionally, the RNA aptamers described herein are water soluble by nature, and generally exhibit nano- to micromolar potency making them potential therapeutic agents for the treatment of neurological disorders involving glutamate receptor activity.

16 Claims, 14 Drawing Sheets
Specification includes a Sequence Listing.

| #0309-3 | CPM/10mg | pmol/10mg |
|---|---|---|
| Forebrain | 8820.4 | 0.085 |
| Hindbrain | 13828.6 | 0.132 |
| Medulla | 11962.2 | 0.115 |
| Cervical | 10334 | 0.099 |
| Thoracic | 4516.4 | 0.043 |
| Lumbar | 1916.8 | 0.019 |

Cervical cord

Lumbar cord

N:nuclear localization,
NC:nucleocytoplasmic,
C:cytoplasmic, Abc:abcence of
TDP-43 IR

SEQUENCE LISTING

```
<160> NUMBER OF SEQ ID NOS: 11

<210> SEQ ID NO 1
<211> LENGTH: 100
<212> TYPE: RNA
<213> ORGANISM: Artificial Sequence
<220> FEATURE:
<223> OTHER INFORMATION: synthetic oligonucleotide

<400> SEQUENCE: 1
gggagaauuc aacugccauc uaggcacgcu acugugagug uugugauggc ggcugaacga      60
ucgaaacgga acuguaguac uacaagcuuc uggacucggu                          100

<210> SEQ ID NO 2
<211> LENGTH: 100
<212> TYPE: RNA
<213> ORGANISM: Artificial Sequence
<220> FEATURE:
<223> OTHER INFORMATION: synthetic oligonucleotide
```

```
<400> SEQUENCE: 2
gggagaauuc aacugccauc uaggcauguu guagacgucu acgucaaacu ccaacgacca    60
gggcauggag uacacaguac uacaagcuuc uggacucggu                        100

<210> SEQ ID NO 3
<211> LENGTH: 25
<212> TYPE: RNA
<213> ORGANISM: Artificial Sequence
<220> FEATURE:
<223> OTHER INFORMATION: synthetic oligonucleotide

<400> SEQUENCE: 3
gggagaauuc aacugccauc uaggc                                        25

<210> SEQ ID NO 4
<211> LENGTH: 25
<212> TYPE: RNA
<213> ORGANISM: Artificial Sequence
<220> FEATURE:
<223> OTHER INFORMATION: synthetic oligonucleotide

<400> SEQUENCE: 4
aguacuacaa gcuucuggac ucggu                                        25

<210> SEQ ID NO 5
<211> LENGTH: 50
<212> TYPE: RNA
<213> ORGANISM: Artificial Sequence
<220> FEATURE:
<223> OTHER INFORMATION: synthetic oligonucleotide

<400> SEQUENCE: 5
acgcuacugu gaguguugug auggcggcug aacgaucgaa acggaacugu              50

<210> SEQ ID NO 6
<211> LENGTH: 50
<212> TYPE: RNA
<213> ORGANISM: Artificial Sequence
<220> FEATURE:
<223> OTHER INFORMATION: synthetic oligonucleotide

<400> SEQUENCE: 6
auguuguaga cgucuacguc aaacuccaac gaccagggca uggaguacac              50

<210> SEQ ID NO 7
<211> LENGTH: 38
<212> TYPE: RNA
<213> ORGANISM: Artificial Sequence
<220> FEATURE:
<223> OTHER INFORMATION: synthetic oligonucleotide

<400> SEQUENCE: 7
ugaauuguuc aaccuugcag aguuuguugg uauggggg                          38

<210> SEQ ID NO 8
<211> LENGTH: 50
<212> TYPE: RNA
<213> ORGANISM: Artificial Sequence
<220> FEATURE:
<223> OTHER INFORMATION: synthetic oligonucleotide

<400> SEQUENCE: 8
gugaguagug auccucauug gcgauuugcc ucggacagcu guccguugag              50
```

```
<210> SEQ ID NO 9
<211> LENGTH: 50
<212> TYPE: RNA
<213> ORGANISM: Artificial Sequence
<220> FEATURE:
<223> OTHER INFORMATION: synthetic oligonucleotide

<400> SEQUENCE: 9
gguaggugau cagcuagaau cucugaaacg gaacuguagu auaaaaaaag                  50

<210> SEQ ID NO 10
<211> LENGTH: 44
<212> TYPE: RNA
<213> ORGANISM: Artificial Sequence
<220> FEATURE:
<223> OTHER INFORMATION: synthetic oligonucleotide

<400> SEQUENCE: 10
gcuugacagc gcauuucacu augcgaggaa ggacguacag caac                        44

<210> SEQ ID NO 11
<211> LENGTH: 82
<212> TYPE: RNA
<213> ORGANISM: Artificial Sequence
<220> FEATURE:
<223> OTHER INFORMATION: synthetic oligonucleotide

<400> SEQUENCE: 11
gggagaauuc aacugccauc uaggcacgcu acugugagug uugugauggc ggcuaacgga       60
acuguaguac uacaagcuuc ug                                                82
```

CHEMICALLY MODIFIED AMPA RECEPTOR RNA APTAMERS

CROSS REFERENCE TO RELATED APPLICATIONS

This application claims the priority of U.S. provisional application No. 62/528,763 filed Jul. 5, 2017; the contents of which are hereby incorporated by reference in their entirety into the present disclosure.

STATEMENT OF RIGHTS UNDER FEDERALLY-SPONSORED RESEARCH

This invention was made with government support under grant number NS060812 awarded by the National Institutes of Health and grant number W81XWH-04-1-0106 awarded by the U.S. Army Medical Research Materiel Command. The government has certain rights in the invention.

SEQUENCE LISTING

This application contains a Sequence Listing, created on Jun. 27, 2018; the file, in ASCII format, is designated 0794160A_SequenceListing_ST25.txt and is 2.38 KB in size. The file is hereby incorporated by reference in its entirety into the application.

BACKGROUND OF THE DISCLOSURE

Glutamate ion channels have three subtypes, i.e., AMPA, kainate and NMDA receptors. Excessive activity of these receptor subtypes either individually or collectively is involved in various neurological disorders. RNA aptamers as antagonists of these receptors are potential therapeutics. For developing aptamer therapeutics, the RNA aptamers must be chemically modified to become ribonuclease-resistant or stable in biological fluids. Using systematic evolution of ligands by exponential enrichment (SELEX) and a chemically modified library, prepared enzymatically (i.e., the library contains RNAs with 2'-fluoro modified nucleoside triphosphates or ATPs, CTPs and UTPs, but regular GTPs), we have isolated an aptamer. The short aptamer (69 nucleotides) FN1040s selectively inhibits the GluA1 and GluA2Q$_{flip}$ AMPA receptor subunits, whereas the full-length aptamer (101 nucleotides) FN1040 additionally inhibits GluK1 (but not GluK2), kainate receptor, and GluN1a/2A and GluN1a/2B, the two major native NMDA receptors. The two aptamers show similar potency (2-4 µM), and are stable with a half-life of at least two days in serum-containing or cerebrospinal fluid making these two aptamers suitable for in vivo use.

Glutamate ion channel receptors mediate the majority of excitatory neurotransmission in the central nervous system (CNS) and are critical for synaptic function and plasticity[1]. Excessive activities and/or elevated surface expression of these receptors, however, have been implicated in a number of neurological disorders, such as stroke, epilepsy, and amyotrophic lateral sclerosis.[1,2] Antagonists of these receptors are therefore drug candidates for treatment of these neurological disorders. To date, most of the drug candidates targeting glutamate ion channels are small-molecule compounds. Low bioavailability due to poor water solubility of these compounds is a major concern in their drug development.[3-7] As a class of water-soluble inhibitors with equal or even better potency compared to small-molecule compounds, RNA-based antagonists or RNA aptamers have been developed by using an in vitro evolution approach, i.e., systematic evolution of ligands by exponential enrichment (SELEX).[8-12] These RNA aptamer are water soluble by nature, and generally exhibit nano- to micromolar potency. One of our aptamers even shows a subunit selectivity.[8] The pharmacological properties of these aptamers rival probably the best of those small molecule inhibitors.

However, unmodified, RNA aptamers are not suitable for in vivo use. This is because natural RNAs are readily degraded in vivo through the ribonuclease-catalyzed cleavage of a phosphodiester bond between each unit of RNA or nucleotide that forms the backbone of an RNA (a phosphodiester bond in a single RNA strand is formed between the 3' carbon atom of one ribose and the 5' carbon atom of another ribose from another nucleoside). Ribonucleases are abundant in biological fluids.[13] For instance, an RNA can be degraded with a half-life ($t_{1/2}$) of a few minutes in human blood.[14] However, chemical modifications of an RNA can prolong its $t_{1/2}$ to minimally a few days.[15,16] The chemical modifications that are proven effective in stabilizing ribonuclease-catalyzed degradation include capping 5'- or 3'-end with polyethylene glycol, replacing the phosphate backbone with a phosphorothioate one, modifying the sugar ring (e.g., the locked nucleic acids), and replacing the 2'-hydroxyl group (2'-OH) with 2'-amino or 2'-fluoro or 2'-0-methyl group.[16] Among these, 2'-fluoro substitution is one of the most effective and frequently used chemical modifications.[14] For example, changing the 2'-OH group to 2'-F on pyrimidines alone could make the RNA sufficiently stable.[17]

SUMMARY OF THE DISCLOSURE

The present disclosure describes chemically modified RNA aptamers that function as AMPA receptor antagonists and are therefore drug candidates for treatment of neurological disorders, such as stroke, epilepsy and amyotrophic lateral sclerosis.

In one aspect, the disclosure relates to a synthetic 2'-fluoro-modified RNA with the primary nucleotide sequence of SEQ ID NO: 1 or truncated versions thereof.

In another aspect, the disclosure relates to a synthetic RNA oligonucleotide consisting of a nucleotide sequence selected from the group consisting of SEQ ID NO: 1, SEQ ID NO: 2 and SEQ ID NO: 11, wherein A, C, and U triphosphates (ATPs, CTPs and UTPs) of said oligonucleotide are 2'-fluoro-modified.

In yet another aspect, the disclosure relates to a synthetic RNA oligonucleotide comprising a nucleotide sequence selected from the group consisting of SEQ ID NO: 1, SEQ ID NO: 2, and SEQ ID NO: 11, wherein A, C, and U triphosphates (ATPs, CTPs and UTPs) of said oligonucleotide are 2'-fluoro-modified. The synthetic RNA oligonucleotides are ribonuclease resistant.

In a related aspect, the disclosure relates to a method for treating neurological diseases and disorders among them stroke, epilepsy and amyotrophic lateral sclerosis using an AMPA receptor antagonist or inhibitor.

In another related aspect, therefore the disclosure relates to a pharmaceutical composition comprising the synthetic modified RNA oligonucleotide described in the disclosure. The pharmaceutical composition may further comprise a pharmaceutically acceptable carrier.

In a further aspect, the disclosure relates to a method for reducing neuropathic pain in a mammal comprising administering a therapeutically effective amount of a synthetic

DETAILED DESCRIPTION

All patents, publications, applications and other references cited herein are hereby incorporated by reference into the present application.

Figures 2A, 2B:
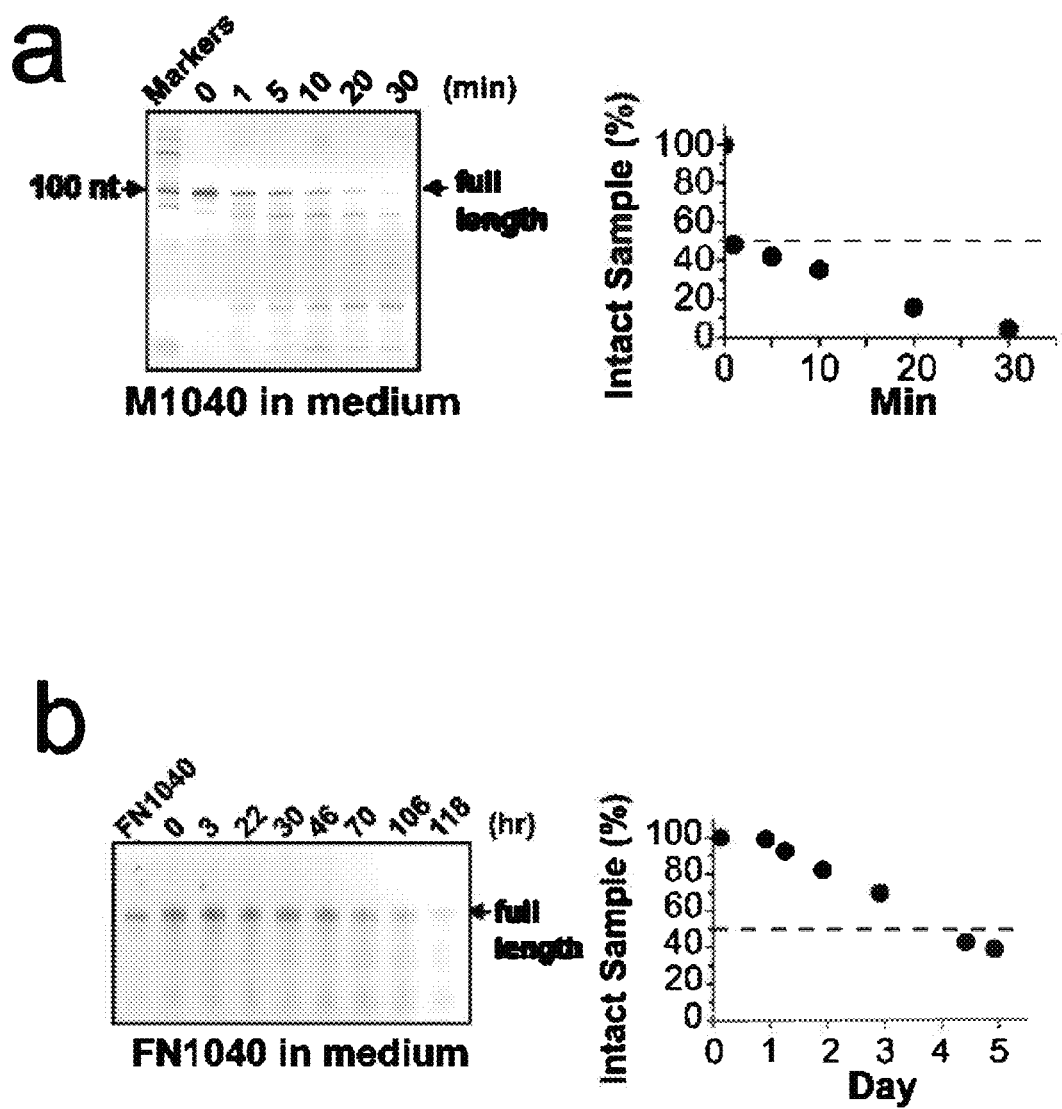
FIGS. 2a-2c show the stability of FN1040 in serum-containing medium and rat cerebrospinal fluid. (a) The RNA was examined by 8 M urea PAGE after incubating with DMEM culture medium supplemented with 10% FBS. RNA Century Markers (Thermo Fisher) were in the left lane. The band intensity of the intact or the full-length RNA was quantified and normalized to the initial sample in the lane labeled as "0" (time zero means that the sample contained no medium or no ribonucleases). The M1040 was the regular RNA and was prepared by transcription reaction using all regular NTPs; M1040 and FN1040 shared the same length and the sequence. The half-life or $t_{1/2}$ of M1040 in cell culture medium is ~1 minute. The dash line marks the 50% degradation level. (b) The $t_{1/2}$ of FN1040 in serum-containing cell culture medium was found to be >3 days. (c) In rat cerebrospinal fluid, the $t_{1/2}$ of FN1040 was ~2.5 days.

Disclosed herein are chemically modified aptamers. In one embodiment, a short aptamer FN1040s (truncated FN1040) selectively inhibits the GluA1 and GluA2Q$_{flip}$ AMPA receptor subunits, whereas another embodiment, the full-length aptamer FN1040, additionally inhibits GluK1 (but not GluK2), kainate receptor and GluN1a/2A and GluN1a/2B, the two major NMDA receptors found in vivo. The two aptamers show similar potency (2-4 µM), and both are considerably ribonuclease-resistant (with a t$_{1/2}$ of at least more than two days). As a comparison, the unmodified M1040, which shares the same oligonucleotide sequence as FN1040, is degraded within minutes (FIG. 2a). Therefore, these modified aptamers are amenable to use in vivo, as intended.

Figures 4A, 4B:
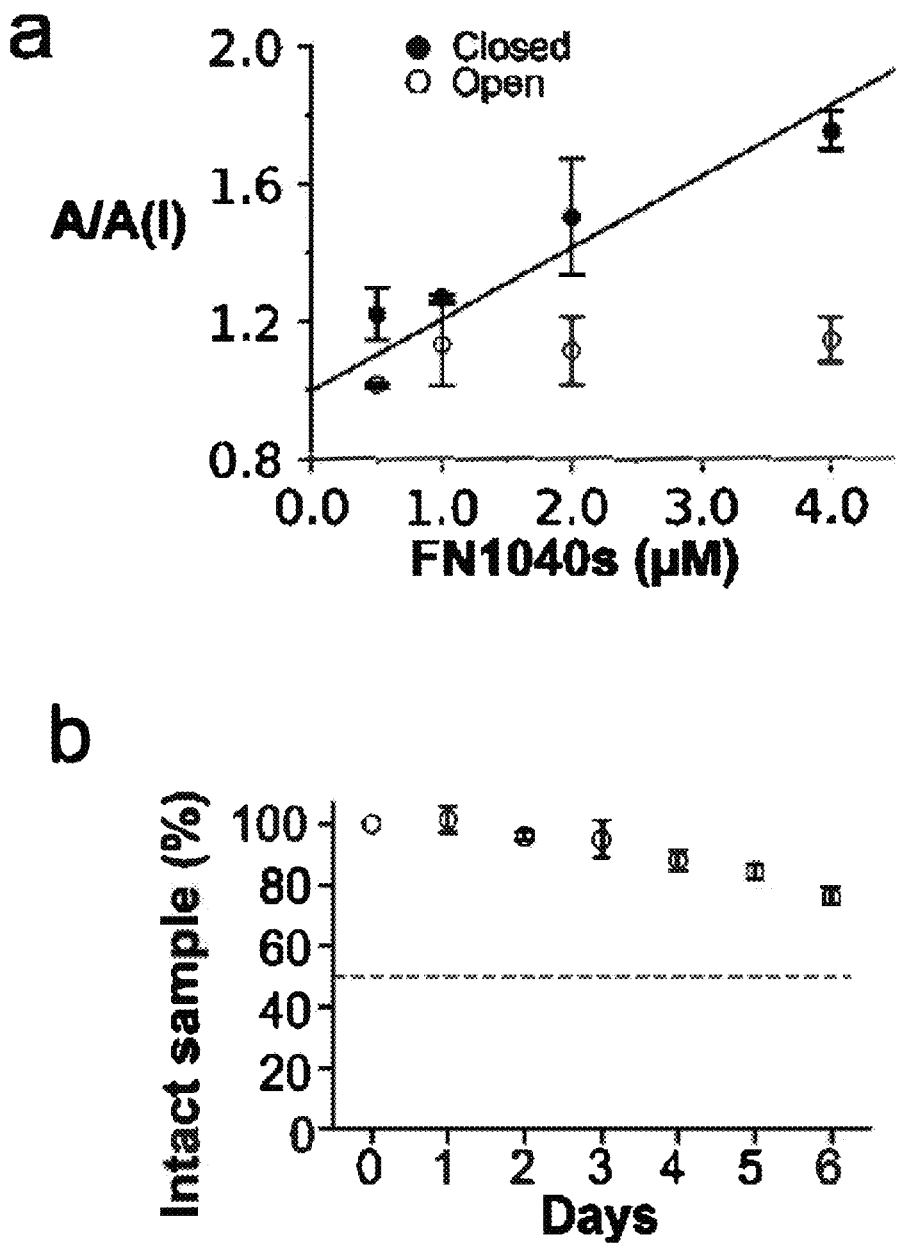
FIGS. 4a-4b depict characterization of the short aptamer FN1040s. (a) FN1040s was tested on GluA2Q receptor at various aptamer concentrations and two glutamate concentrations (hollow circle, open channel, 3 mM; solid circle, closed channel, 0.1 mM glutamate). The $K_I$ was estimated to be 4.8±0.5 µM using eq 1, for the closed-channel conformation (closed circle). (b) The stability of FN1040s was examined by incubating with mammalian cell culture medium, i.e., DMEM with 10% FBS, at 37° C. After 6 days of exposure to this medium, >75% of FN1040s remained intact. Dash line shows the 50% degradation level.
Figure 7:
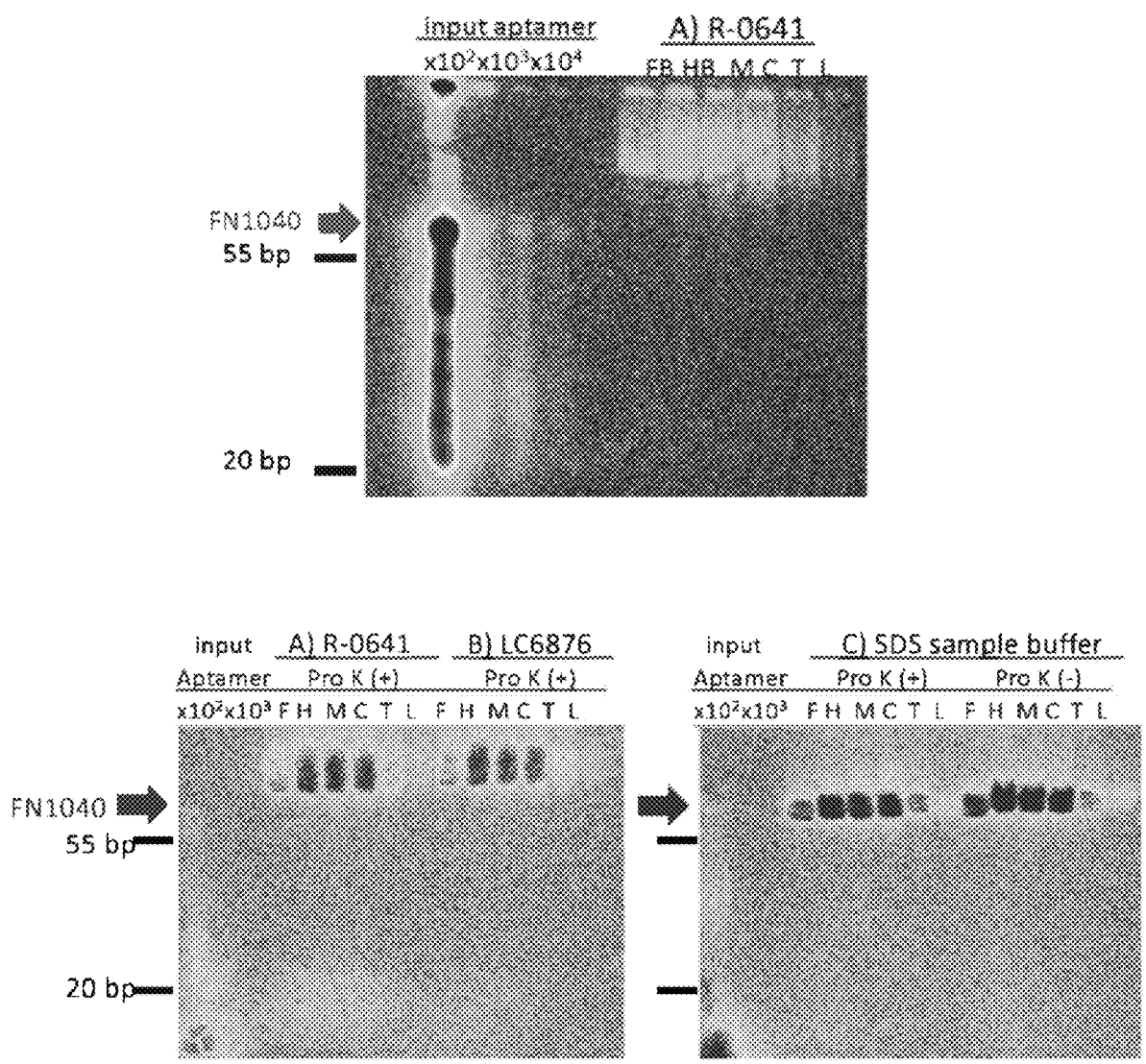
FIG. 7 shows that FN1040 was stable in the mouse spinal cord for at least 3 days, based on the estimate of the radioactivity of $^{32}$P-labeled FN1040. The lanes labeled by F, H, M, C, T and L are aptamers isolated from forebrain, hindbrain, medulla, cervical, thoracic and lumber tissues, respectively. We also used proteinase K (Pro K) in our assays. Proteinase K itself is a protein, and is resistant to denaturation by heat, detergents, and chaotropic salts. The presence and absence of this protein shows that aptamer was stable and distributed almost equally within the spinal cord.
Figure 8:
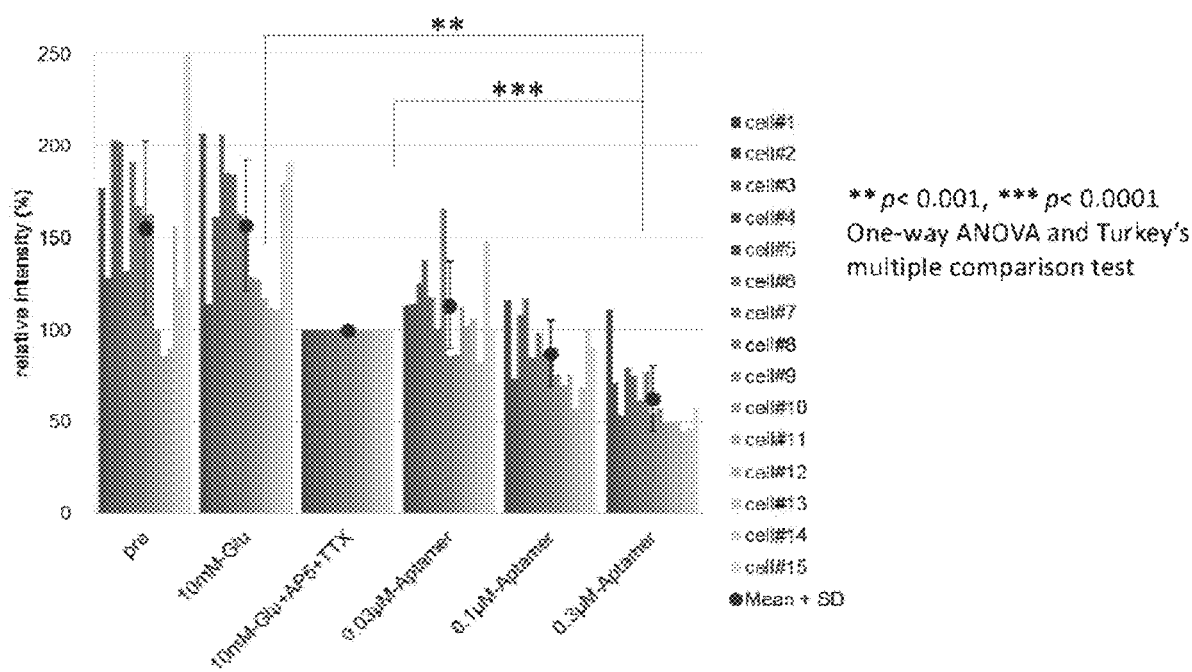
FIG. 8 shows that FN1040 at concentrations greater than 0.1 µM effectively blocked Ca$^{2+}$ influx in cortical neurons that expressed Q/R site-unedited GluA2 of ADAR2$^{flox/flox}$ mice. Ca$^{2+}$ influx was monitored using Ca$^{2+}$-sensitive dye on a two-photon microscope. Specifically, live neurons (n=15) were observed under two-photon microscope for one day. AAV-Syn1-GCaMP ($1\times10^{11}$ vg/ml, 2 µl) and AAV-CMV-Cre ($2\times10^{12}$ vg/ml, 2 µl) were injected 20 days before imaging into mouse retrosplenial cortex (A/P; −2.0 mm, M/L; 0.6 mm from bregma, D/V; 1 mm). As seen, FN1040 at >0.1 µM was able to effectively block $Ca^{2+}$ influx in cortical neurons that express Q/R site-unedited GluA2 of ADAR2$^{flox/flox}$ mice. One-way ANOVA and Tukey's multiple comparison tests were used.  $p<0.001$, * $p<0.0001$.
Figure 9:
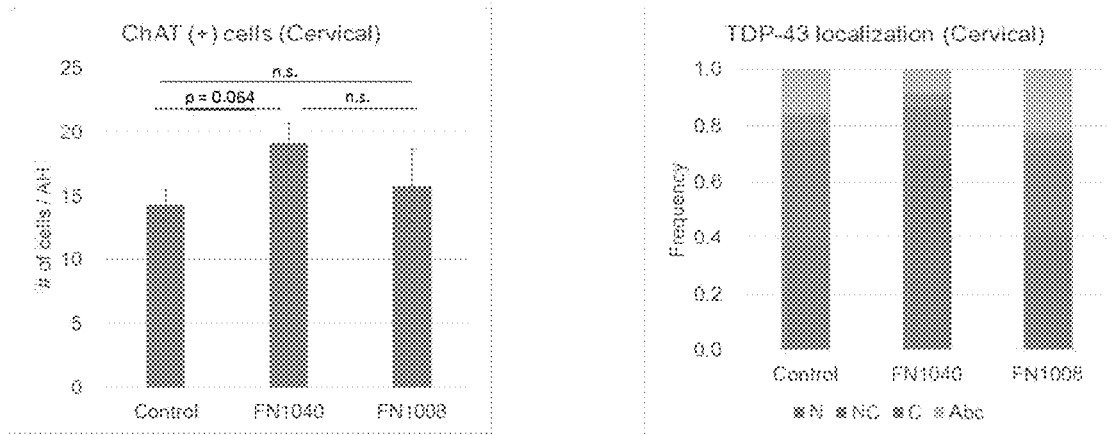
FIG. 9 shows in vivo effects of FN1040 and FN1008 on the spinal motor neurons of AR2 mice in a 36-day continuous icy administration. The upper two panels are for cervical cord and the low two panels are for lumbar cord. N, NC, and C represent nuclear, nucleocytoplasmic, and cytoplasmic localization, respectively, while Abc means "absence of TDP-43". No of AR2 Mice: control, n=3; FN1040, n=3; FN1008, n=2; 22 weeks old. Control was injected with aCSF. Aptamer was used at 10 µM concentration. Protocol: the 36-day administration was divided into 9 sets. Each set is a 4-day run; in each 4-day period, 1.0 µl/hr×3 days+0.1 µl/hr×1 day. Our data shows that FN1040, but not FN1008, significantly improved TDP-43 mislocalization in the motor neurons in the spinal anterior horn of ADAR2$^{flox/flox}$/ VAChT-Cre (AR2) mice. FN1040 effectively ameliorated exaggerated $Ca^{2+}$ influx through the Q/R site-unedited GluA2-containing AMPA receptors and rescued dying motor neurons. Notably, FN1040 lacked sedative effects on the mice. As a comparison, perampanel, a small-molecule AMPA receptor inhibitor, showed similar neuroprotection; but perampanel causes significant sedative effects on the mice which was tested using the same approach.
Figure 9:
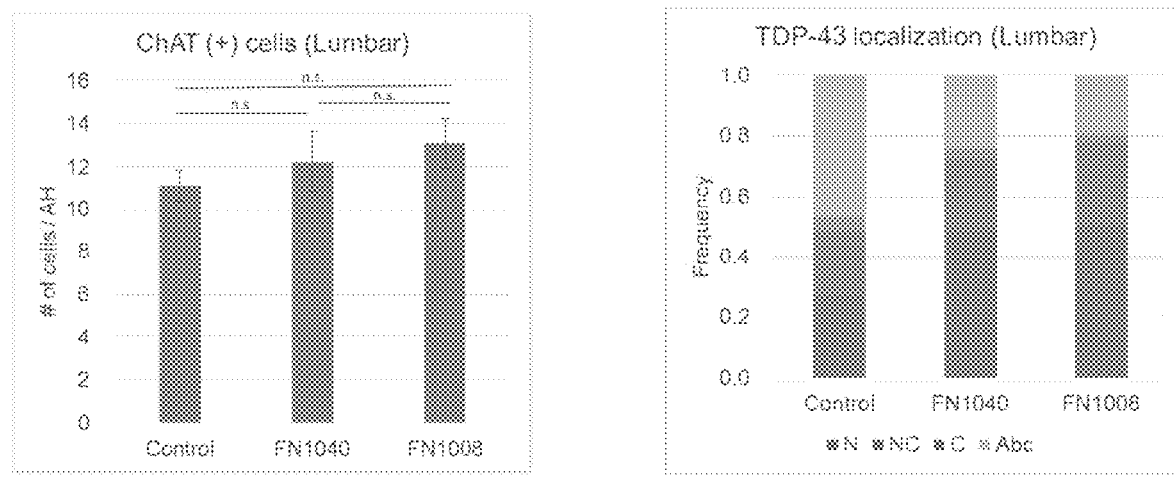
Figure 10:
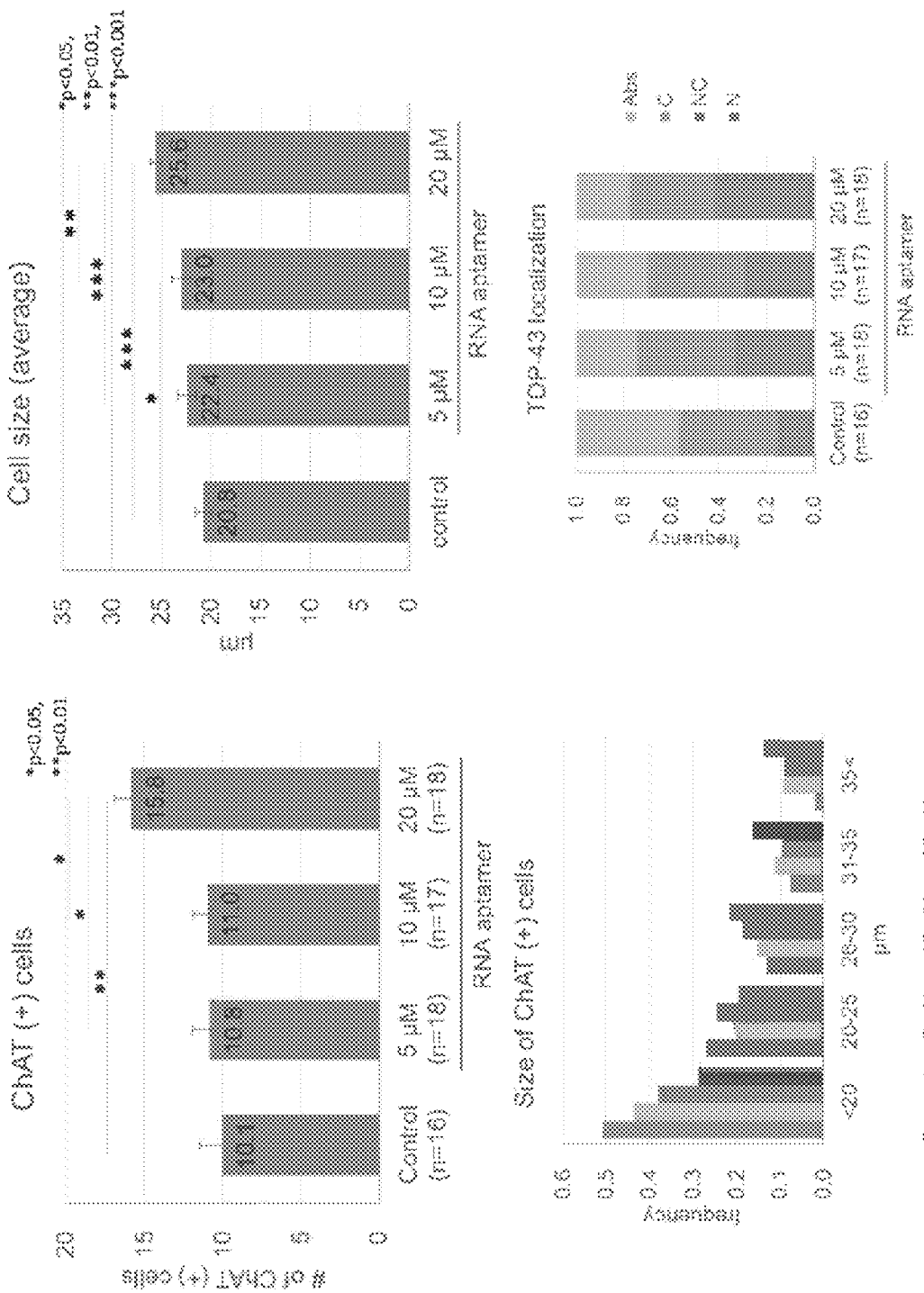
FIG. 10 ChAT refers to choline acetyltransferase, the enzyme catalyzing the formation of acetylcholine. An immunocytochemical assay using anti-ChAT antibody is a commonly used specific marker of cholinergic structures within the nervous tissue (Fonnum F. (1973: Recent developments in biochemical investigations of cholinergic transmission. Brain Research, 62, 497-507). In this experiment, ChAT staining is used as the motor neuron marker. Therefore, live motor neurons are stained with the anti-ChAT antibody. As seen, the aptamer shows a dose-dependent rescue of motor neurons in both the cell number (let panel on the upper row) and the cell size (right panel on the upper row and the left panel on the lower row), as compared with those from AR2 mice. The TDP-43 assay is the same as FIG. 9.

Modified FN1040 aptamers show a better stability or t$_{1/2}$ than pegaptanib sodium, MACUGEN®, a clinically used RNA aptamer drug for treatment of macular degeneration[40, 41]. MACUGEN® has a half-life of 9.3 hours in serum.[42] MACUGEN® is a 27-nt long RNA with 40 kDa PEG conjugated at the 5'-end. Among those 27 nucleotides, only two nucleotides (or 7% of its nucleotide positions) are unmodified. In contrast, FN1040 contains 30 regular nucleotides (i.e., Gs) in the overall 100-nt length; in other words, 30% of the sequence positions are unmodified. Yet, FN1040 is more stable than MACUGEN®. In fact, the short aptamer FN1040s is more than twice as stable as its predecessor FN1040 (FIGS. 4b vs. 2b). The stability results show that FN1040 and FN1040s are suitable for in vivo use even without any further chemical modification. It should be noted, however, that the in vitro stability values we have determined for the two aptamers can be used as a guide for in vivo study. In an in vivo study (e.g., an animal study), the stability of each of these aptamers is assessed, which can be carried out by using a radiolabeled RNA aptamer as presented here—see FIG. 7a-7c. Furthermore, the stability of the aptamers can be further improved. For example, solid-state synthesis can be used to make the same RNA aptamer by additionally replacing Gs.

It is interesting to note that the full-length FN1040 and the short FN1040s possess differential selectivity towards various glutamate receptor subunits. FN1040 is selective to GluA1 and GluA2Q$_{flip}$ AMPA receptor subunits, whereas FN1040 shows a broad ability to block glutamate receptor activities. At the present, the origin by which the short aptamer gains selectivity or shows a narrower range of antagonism is unknown. The two aptamers most likely bear similar branched structures (at least as predicted by the MFold; see FIG. 3). However, the smaller size of FN1040s could be more important. It is conceivable that unlike a small-molecule inhibitor that binds to a cavity site, an RNA may bind to a surface-dominant site. RNA binding to and interaction with a receptor site generally involve complex molecular interactions of many nucleotides with many amino acids over multiple contact points.[33, 34] Without wishing to be bound by theory, it is thought that the full-length RNA may cover a larger area shared, at least in part, by many subunits in the glutamate receptor family. The short aptamer loses some of these contact points, and therefore becomes less capable of broadly interacting with a large set of similar subunits. In turn, it becomes more capable of selectively interacting with a limited number of subunits; in this case, FN1040s becomes GluA1 and GluA2 selective.

With a sufficient in vitro stability, the two chemically modified aptamers can be used in various settings. For example, short FN1040s can be used to preferentially block the GluA1 AMPA receptor subunit, a major AMPA receptor subunit in the hippocampus.[43, 44] Currently, there is no small-molecule antagonist to selectively probe the activity of GluA1 in vivo. The full-length aptamer FN1040 can be used to test the therapeutic utility of blocking glutamate receptor subunits in controlling neuropathic pain, as an example. In this regard, NMDA receptors,[45] kainate receptor or precisely GluK1[46] and AMPA receptors[47] have all been implicated in mediating neuropathic pain. Therefore, blocking these receptor subtypes altogether provides a viable therapeutic approach for a potential treatment of neuropathic pain.

Preparation of Modified Aptamers

There are two ways to prepare 2'-fluoro modified RNA aptamers. First, a useful aptamer that has been identified already through SELEX can be subject to sequence-based nucleotide replacement or post-SELEX modification. For example, a 2'-F containing RNA can be prepared by enzymatic transcription using the same DNA template but with 2'-F nucleotides. However, a chemically modified RNA with the sequence identical to its unmodified RNA aptamer could have a very different structure and consequently a much attenuated potency, as compared with the canonical RNA.[18-20] The second approach is generally more desirable, and sometimes inevitable, in which SELEX is used with a chemically modified library to isolate a chemically modified aptamer—the chemical modifications are introduced to the library or "pre-SELEX". By this approach, a chemically modified RNA aptamer with the best fitted structure from a large RNA library (e.g., ~$10^{15}$ sequences with a 100 nucleotide binding sequence)[21] could be selected without compromising the potency.[16]

Here, the isolation and the characterization of a 2'-fluoro modified RNA aptamer is disclosed. This aptamer contains 2'-F group in the sugar ring of A, C, U nucleoside positions (i.e., adenosine, cytidine and uridine), and has been isolated from an RNA library in which all RNAs are 2'-fluoro modified at the three positions. The full-length (100-nt) RNA aptamer was also truncated to a short (69-nt) but functional aptamer. We have also screened the aptamers against all glutamate ion channel subtypes, which include α-amino-3-hydroxy-5-methyl-4-isoxazole (AMPA), kainate and N-methyl-D-aspartate (NMDA) receptors, and their subunits. The full-length aptamer is capable of blocking all three glutamate receptor subtypes. In contrast, the shortened aptamer is AMPA receptor selective. Specifically, the short aptamer is selective to GluA1 and GluA2 AMPA receptor subunits without appreciable activity on GluA3 and GluA4, the remaining two AMPA receptor subunits. We found that the potency of these two aptamers is 2-4 µM. Both aptamers are stable, with a half-life ($t_{1/2}$) of at least 2 days, as in the serum solution and rat cerebrospinal fluid (CSF). Therefore, these two aptamers are amenable for in vivo use.

In one embodiment, an RNA aptamer of the disclosure has the nucleotide sequence of SEQ ID NO: 1.

In yet another embodiment, an RNA aptamer of the disclosure has the nucleotide sequence of SEQ ID NO: 2.

In yet another embodiment, an RNA aptamer of the disclosure has the nucleotide sequence of SEQ ID NO: 11.

Experimental Design.

To find a 2'-fluoro modified aptamer from 2'-fluoro modified RNA library by using SELEX, we designed the following experiment. First, in our library, all RNAs are 100 nt in length with a randomized region containing 50 nucleotides (N50) in the middle (see Table 1). For making an RNA library (~$10^{14}$) with 2'-fluoro modifications, all U, A and C positions were chemically modified, but all G (guanine) positions contained the regular, unmodified Gs. This was because the enzymatic transcription reaction required that the first two nucleotides after the promoter site be GG (or CC in the template strand; the first G is required and the second G gives higher yield of transcription) for transcription initiation.[22] Bases other than regular Gs in these two positions may prevent the transcription reaction from starting or lead to significantly lower yields.[23, 24] Second, for RNA transcription using non-canonical 2'-F NTPs (i.e., "N" in the "NTP" stands for A, C and U), we used a mutant T7 RNA polymerase (Y639F/H784A).[25] This mutant polymerase has a much better processivity in incorporating non-canonical NTPs.[26] The use of this enzyme was critical because of the intrinsic low efficiency or low yield in transcribing a chemically modified RNA. It should be further noted that the modification of all A, C, U, but not G, positions ensured a maximum, putative stability, since in general, the more of the nucleotides in an RNA that are chemically modified, the more stable the RNA becomes.[27]

Enzymatic Transcription for Preparing 2'-Fluoro Modified RNA Library.

By using the mutant T7 RNA polymerase (Y639F/H784A) with 2'-fluoro NTPs (i.e., 2'-F-A, 2'-F-C, and 2'-F-U), we carried out the transcription reaction for preparing the 2'-fluoro modified RNA library. The transcription reaction generated >70% of the yield for the library, as compared with the reaction with all regular NTPs and the use of the wild type T7 RNA polymerase.[9] We note that incorporation of 2'-fluoro-GTP in the transcription using Y639F/H784A failed, consistent with the critical requirement of regular G in transcription initiation.[22] Furthermore, using the Y639F T7 RNA polymerase, instead of the Y639F/H784A mutant, we only observed <10% yield of incorporating 2'-fluoro modified As, Cs and Us.[26, 28] The final full-length transcript of the randomized RNA library reached a concentration of up to ~45 µM in the reaction mixture. The modified RNA library was purified by polyacrylamide gel electrophoresis (PAGE) before SELEX. In each of the following rounds of the SELEX operation, a 2'-fluoro modified RNA library was similarly transcribed and purified.

Discovery of FN1040 by In Vitro Selection.

A total of 12 cycles or rounds of SELEX were performed in pursuit of RNAs that bind to the target, GluA2Q$_{flip}$ receptors in HEK-293 cell membrane fragments. Among them, rounds 4 and 9 were negative selections in which plain cell membrane fragments were used to "absorb" nonspecific RNAs in the library in order to suppress nonspecific RNAs during the in vitro evolution. After 12 rounds, the DNA libraries from rounds 10, 11, and 12 were cloned to pGEM-T easy vector, and sequenced. From the 100 sequences (i.e., 30, 38 and 32 clones from rounds 10, 11 and 12, respectively), six sequences were identified with multiple copies and 15 single-copy sequences (Table 1).

TABLE 1

Sequences from in vitro selection and primary functional screening by whole-cell recording on GluA2Q$_{flip}$

| Sequence name | SEQ ID NO. | Sequence in random region[a] | % | A/A(I) |
|---|---|---|---|---|
| FN1040[b] | 5 | ACGCUACUGUGAGUGUU GUGAUGGCGGCUGAACG AUCGAAACGGAACUGU | 56% | 1.6 ± 0.2 |
| FN1008 | 6 | AUGUUGUAGACGUCUAC GUCAAACUCCAACGACC AGGGCAUGGAGUACAC | 13% | 1.2 ± 0.2 |
| FN1140 | 7 | UGAAUUGUUCAACCUUG CAGAGUUUGUUGGUAUG GGGG | 6% | 1.2 ± 0.1 |
| FN1203 | 8 | GUGAGUAGUGAUCCUCA UUGGCGAUUUGCCUCGG ACAGCUGUCCGUUGAG | 3% | 1.1 ± 0.1 |
| FN1138 | 9 | GGUAGGUGAUCAGCUAG AAUCUCUGAAACGGAAC UGUAGUAUAAAAAAAG | 2% | 1.0 ± 0.1 |
| FN1209 | 10 | GCUUGACAGCGCAUUUC ACUAUGCGAGGAAGGAC GUACAGCAAC | 2% | 1.1 ± 0.1 |

[a]5'-side and 3'-side constant region sequences are 5'-GGGA-GAAUUCAACUGCCAUCUAGGC-3' (SEQ ID NO: 3) and 5'-AGUACUACAAGC-UUCUGGACUCGGU-3' (SEQ ID NO: 4), respectively.
[b]RNAs were tested at 1 µM concentration; glutamate was 100 µM.

The percentage of these repeating sequences in the last three rounds showed that the 12-round evolution reached to a stable stage (Table 2).

TABLE 2

The percentage of sequences in each of the last three rounds

| Sequence Name | Round | | |
|---|---|---|---|
| | 10 | 11 | 12 |
| FN1040 | 64% | 61% | 44% |
| FN1008 | 4% | 18% | 16% |
| FN1140 | 4% | 5% | 9% |
| FN1203 | 7% | ND | 3% |
| FN1138 | ND | 5% | ND |
| FN1209 | ND | 3% | 3% |

ND, not detected.

Functional Characterization of FN1040 by Whole-Cell Recording.

Figure 1A:
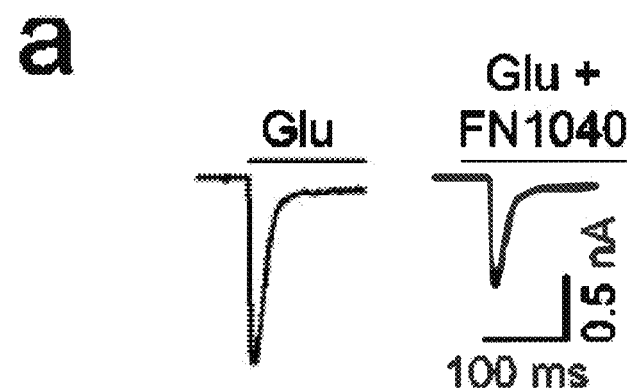
FIGS. 1a-1d show that FN1040 inhibits GluA2Q receptor. (a) FN1040 inhibited GluA2Q-mediated whole-cell current response to 0.1 mM glutamate (right), as compared to the control (left). The bar on top of a trace shows the time course of glutamate exposure with and without FN1040 (at 2 µM). The desensitization constant $k_{des}$ measured with and without FN1040 were 51±9 s$^{-1}$ and 54±5 s$^{-1}$, respectively. A two-sample two-tailed Student's t-test showed no difference between the two means with p=0.50. (b) Effect of FN1040 on the closed-channel conformation (solid circle, measured at 0.1 mM glutamate) and the open-channel conformation (open circle, measured at 3 mM glutamate). An inhibition constant $K_I$ was determined to be 2.3±0.7 µM for the closed-channel conformation using eq 1 (see Data Analysis of Whole-Cell Current Amplitude). (c) The binding affinity ($K_d$) of FN1040 on GluA2Q, determined using homologous competitive binding assay was estimated to be 20±4 nM using eq 2 (see Homologous Competitive Binding Assay). Each data point in the plot was an average of at least 3 measurements. Standard deviation from the mean is shown. It should be noted that the nonspecific binding signal with plain HEK-293 cell membrane was 50-80 CPM. (d) Glutamate, NBQX, BDZ-g, and BDZ-f were used to compete with the $^{32}$P-labeled or hot FN1040 in the binding reaction with GluA2Q. The cold FN1040 was used as a control to compete with hot FN1040 in order to determine the background binding. The radioactivity was normalized to the reaction that contained only the hot FN1040.
Figure 1B:
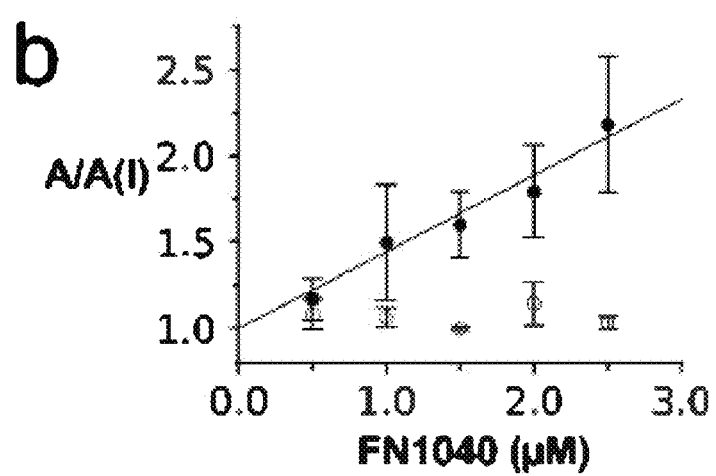

Using whole-cell current recording, we first tested each of the six putative RNA aptamers against GluA2Q$_{flip}$, the SELEX target. We found that FN1040 inhibited the whole-cell current amplitude of the GluA2Q$_{flip}$ channel (FIG. 1a) with an A/A(I) value of 1.6±0.2 (Table 1), suggesting FN1040 is an inhibitor. Further studies of FN1040 showed that it selectively inhibited the closed-channel form of GluA2Q$_{flip}$ but not the open-channel form (FIG. 1b). To verify this, we tested the aptamer at increasing concentrations against the GluA2Q$_{flip}$ channel expressed in HEK-293 cells (FIG. 1b). On the closed-channel conformation, we observed a linear relationship between the A/A(I) value and the aptamer concentration (FIG. 1b). Using eq 1 (see Data Analysis of Whole-Cell Current Amplitude), we estimated that the inhibition constant, K, for the closed-channel form of GluA2Q$_{flip}$ was 2.3±0.7 µM (FIG. 1b). However, FN1040 did not inhibit the open-channel conformation, as the A/A(I) values for the open-channel conformation of the GluA2Q$_{flip}$ receptor remained ~1.0 even when the concentration of the aptamer was increased.

Binding Affinity of FN1040 on GluA2Q$_{flip}$.

Figure 1C:
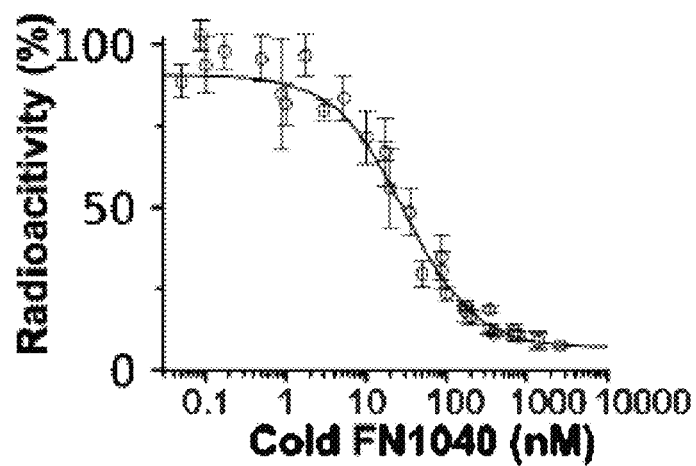

The binding affinity, K$_d$, of FN1040 for GluA2Q$_{flip}$ was estimated from a homologous competitive binding experiment. In this experiment, intact GluA2Q$_{flip}$ receptors embedded in HEK-293 cell membrane fragments were mixed with $^{32}$P-labeled or hot FN1040 (see RNA 5'-end Labeled with $^{32}$P.). The unlabeled FN1040 (or cold FN1040) was used to compete with the hot FN1040 for the binding to GluA2Q$_{flip}$ receptors. As shown, the normalized radioactivity as a function of the cold FN1040 was determined (FIG. 1c). The K$_d$ value was estimated to be 20±4 nM by nonlinear fitting of the binding data using eq 2 (see Homologous Competitive Binding Assay).

Figure 1D:
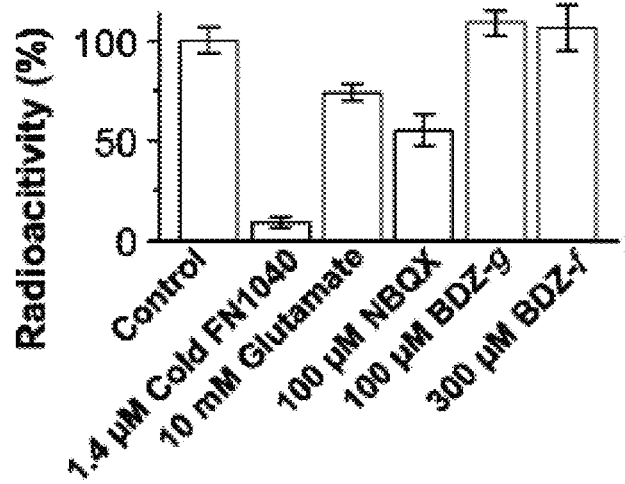

FN1040 was the dominant sequence evolved from the SELEX experiment in which a mixture of AMPA receptor inhibitors with known mechanisms of action were used to elute RNA. The inhibitors included NBQX, a competitive inhibitor,[29] and two 2,3-benzodiazapine derivatives, BDZ-f and BDZ-g, which are noncompetitive antagonists of AMPA receptor.[30] All chemicals were used at saturating concentrations to elute RNAs that might have bound to the same sites or mutually exclusive sites during SELEX. In the homologous competitive binding experiment, we used the same compounds, one at a time, to compete with the hot FN1040 in order to gain an understanding about the site of interaction for FN1040. As seen (FIG. 1d), either BDZ-f or BDZ-g, the two noncompetitive inhibitors, was ineffective in displacing hot FN1040. NBQX, however, was capable of displacing ~50% of the hot FN1040 (FIG. 1d) (note K$_d$ of NBQX with the partial ligand binding domain or S1S2 of GluA2 receptor is ~20 nM; in our experiment, we used 100 µM).[31] This result suggested that FN1040 is most likely a competitive inhibitor. Consistent with this notion is the fact that NBQX, a competitive inhibitor, was part of the inhibitor mix for RNA elution during SELEX, and glutamate was also capable of competing with hot FN1040 to bind to the receptor, albeit less effectively, as compared with NBQX (FIG. 1d) (in this case, glutamate at 10 mM, a saturating concentration, reduced ~30% of bound FN1040). It should be noted that when glutamate was used for the binding assay, the receptor was in the desensitized state, since glutamate desensitizes the GluA2Q$_{flip}$ on a millisecond time scale.[32] The fact that FN1040 did not inhibit the GluA2Q$_{flip}$ receptor (open channel) at the 3 mM glutamate concentration (FIG. 1b), where the concentration of glutamate was much higher than that of aptamer, was further consistent with the notion that FN1040 inhibited GluA2Q$_{flip}$ competitively. However, we do not know why NBQX even at saturating concentration was only partially effective in competing with the binding of FN1040 to the receptor. One possibility is that unlike a small-molecule compound, which usually binds to a pocket of a well-folded protein, an RNA binding to and interacting with a protein target generally involve interactions of many nucleotides on RNA with many amino acids on the protein target over multiple contact points or sites.[33, 34]

Stability of FN1040 in Rat Cerebrospinal Fluid and Serum-Containing Cell Culture Medium.

Figure 2C:
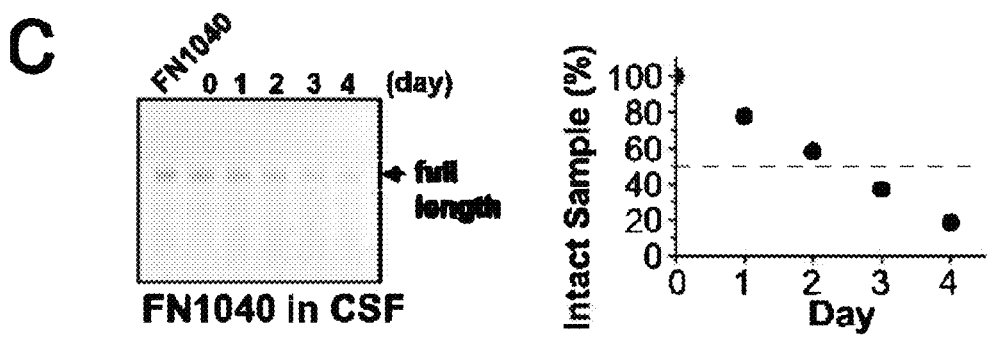

The putative stability of FN1040 was assessed in two types of ribonuclease-containing media, i.e. rat CSF and HEK-293 cell culture medium (DMEM or Dulbecco's Modified Eagle's Medium) supplemented with 10% fetal bovine serum. DMEM was routinely used in HEK-293 cell culture and readily available in our experiment. CSF would represent an environment where the aptamer would be directly delivered to CNS as a potential drug candidate. Both types of biological fluids are known to contain ribonucleases.[13] As shown (FIG. 2a), unmodified or regular RNA control (M1040) had a $t_{1/2}$ of just about one min at 37° C.; the control was degraded completely in ~30 min. In contrast, the modified RNA or FN1040 showed a $t_{1/2}$ of ~3.5 days (FIG. 2b). It should be noted that M1040 and FN1040 have the identical RNA sequence, but the control contains regular NTPs. Similarly, FN1040 was incubated in rat CSF at 37° C., and under this condition, FN1040 was found to have a $t_{1/2}$ of ~2.5 days (FIG. 2c). These results have clearly illustrated that by replacing 2'-OH group with 2'-F atom on all A, C and U positions, the stability of the RNA aptamer or the resistance to ribonuclease-catalyzed degradation has been significantly improved. Incidentally, the $t_{1/2}$ values of FN1040 in both serum-containing cell culture medium and rat CSF were roughly similar (FIGS. 2b and 2c). This result therefore suggested that the $t_{1/2}$ value obtained from the serum-containing cell culture medium in this case could serve as a reliable measure of how stable the same aptamer would be in rat CSF. This is useful, because the cell culture medium is much more readily available.

Truncation of FN1040 for Identification of a Shortened Functional Aptamer

Figure 3:
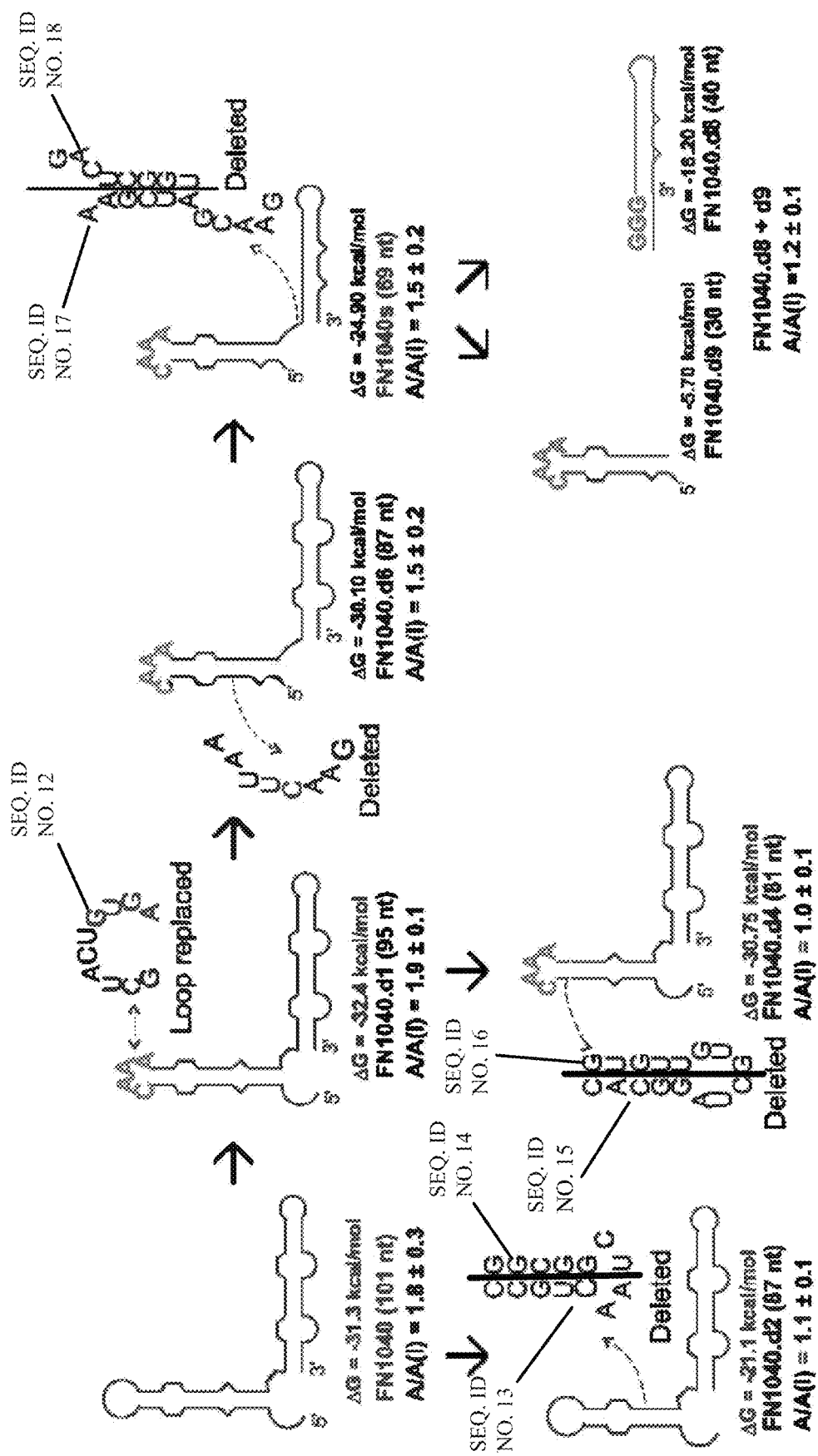
FIG. 3 shows the sequence truncation of FN1040 and functional test of the shortened RNAs. The sequence of FN1040 was truncated or replaced to a series of shortened RNAs (from FN1040.d1 to FN1040.d9), as shown. The 2D structures predicted using the Mfold program are simplified to shapes drawn by lines. Paralleled lines indicate base-pairing stems. A triangle turn represents a single nucleotide bulge. The stick out square with two corners represents two unpaired nucleotides. Whole-cell current recording was used for functional assay with GluA2Q$_{flip}$ receptor expressed in HEK-293 cells. In all the tests, 2 µM aptamer and 0.1 mM glutamate were used. A/A(I) values are shown. Note that the d8 and d9 samples, which represented the split of the two branches of the FN1040s aptamer, were mixed with 2 µM of each for the assay.

FN1040 was shortened in order to identify a functional aptamer with a minimal length. By removing any non-essential nucleotides, a short aptamer would be more economical to produce and potentially more stable. Before truncation, we used Mfold program[35] to make some predictions about secondary structures (2D) of FN1040 (FIG. 3). It should be noted, however, that the Mfold program is for predicting RNA canonical and wobble base-pairing. Currently, there is no program for predicting secondary structures of chemically modified RNAs. The structural prediction may be somewhat meaningful, because the 2'-fluoro modification was made in the sugar ring, and the 2'-fluoro modified RNA may have stronger H-bonding in Watson-Crick base-pairing and also stronger stacking interaction as compared with regular RNA.[36] Nonetheless, the Mfold-generated 2D structural features for FN1040 were considered, at best, primitive clues.

On the basis of a branched secondary structure of the 100-nt FN1040 (FIG. 3), first the G28-A37 (SEQ ID NO: 12) section, predicted as a loop, was replaced with a "CAAA" tetra-loop motif (this 95-nt RNA was named as FN1040.d1) (FIG. 3). The RNA was prepared in 2'-fluoro modified form, purified, and tested on GluA2Q receptor expressed in HEK-293 cells using whole-cell recording. The ratio of the current amplitude in the absence and presence of the aptamer or A/A(I) was found to be 1.9.+-.0.1, identical to the A/A(I) value of 1.8.+-.0.3 of the full length FN1040 (FIG. 3). This result suggested that a large loop in the wild-type RNA was not essential for function. However, shortening either the lower portion of the base-paired stem of the first branch, i.e. A11-C17 (SEQ ID NO: 13) and G48-U54 (SEQ ID NO: 14) (FN1040.d2), or the upper portion of the first branch by deleting C20-C27 (SEQ ID NO: 15) and G38-G45 (SEQ ID NO: 16) (FN1040.d4) resulted a nonfunctional RNA.

In contrast, removing G5-A12 (SEQ ID NO: 19) in FN1040.d1, resulting FN1040.d6, largely kept the inhibitory function (A/A(I)=1.5.+-.0.2). On the second branch, deleting two large segments, i.e. G55-A64 (SEQ ID NO: 17) and G94-U101 (SEQ ID NO: 18), yielded a 69-nt aptamer or FN1040s, which did not affect significantly the inhibitory function (A/A(I)=1.5.+-.0.2). Overall, FN1040s was 30% shorter than the full-length FN1040, and, by the Mfold prediction, FN1040s maintained a similar branched structure. However, when the branched structure was disconnected, yielding two separate RNAs (i.e., FN1040.d8 and FN1040.d9), an equal molar mixture of the two virtually lost the inhibition (FIG. 3). Therefore, FN1040s was considered a functional, but short aptamer. The size of FN1040s falls into a general range of the minimized aptamers previously reported.[8-10, 37, 38]

The properties of FN1040s, as compared with the full-length FN1040 aptamer were further verified. The inhibitory property of FN1040s was estimated from a series of aptamer concentrations against GluA2Q$_{flip}$, the SELEX target. The $K_I$ of 4.8±0.5 µM was obtained (FIG. 4a). As compared with FN1040 (FIG. 1b), the $K_I$ value appeared to be slightly higher. Like FN1040, the short aptamer only inhibited the closed-channel conformation of the GluA2Q$_{flip}$ receptor (FIG. 4a). However, FN1040s showed a stronger stability or resistance to ribonuclease digestion in serum-containing culture medium in that >80% of FN1040s remained intact even after 4 days at 37° C. (FIG. 4a). As a comparison, only ~50% of full-length FN1040 remained after the same time period (FIG. 2b).

Subunit Selectivity of FN1040s and the Full-Length FN1040

Figure 5A:
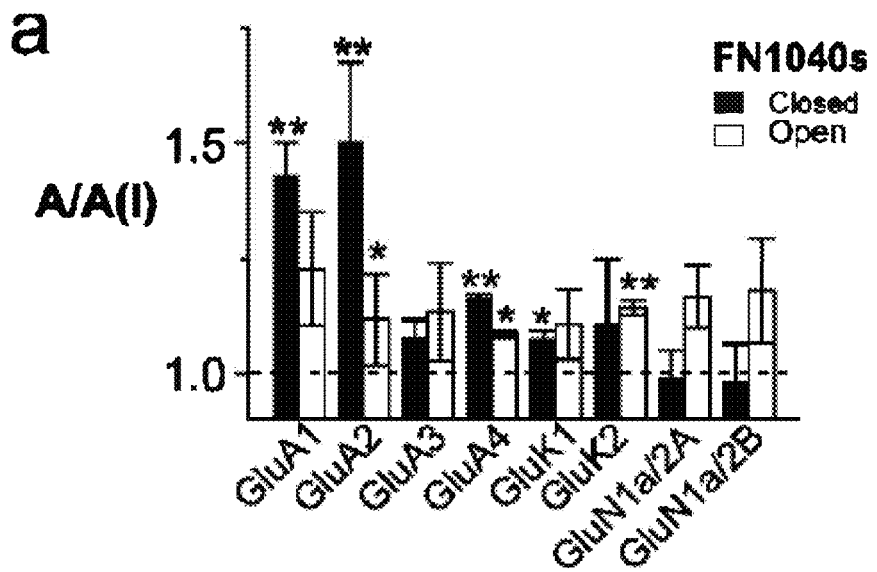
FIGS. 5a-5b show the selectivity of the short aptamer FN1040s (a) and the full-length aptamer FN1040 (b). The selectivity was measured in the A/A(I) value using the same aptamer concentration (2 µM) against the subunit and channel types in the glutamate ion channel family. The glutamate concentrations used for closed-channel (solid columns) and open-channel (hollow column) conformation (in mM) were 0.05 and 3 for GluA1, 0.1 and 3 for GluA2 and GluA4, 0.5 and 20 for GluA3, 0.05 and 3 for GluK1 and GluK2, and 0.02 and 0.05 for GluN1a/2A and GluN1a/2B, respectively. (a) One-sample two-tailed Student's t-tests on each column were performed with H$_0$: µ=µ$_0$=1, 1 being the theoretical value of no inhibition (p≤0.5). The significance of the Student's t-test for each column was labeled as the double asterisk (p≤0.1) or the single asterisk (p≤0.5). Further, a one-way ANOVA analysis combining with post hoc Tukey's test indicated that the mean A/A(I) value of FN1040s on closed-channel conformation of GluA2Q receptor was different when comparing to other receptors on the closed-channel conformation at p≤0.05, except for closed-channel conformation of GluA1. The mean A/A(I) value of FN1040s on the closed-channel conformation of GluA1 was different from all but the closed-channel conformation of GluA2 and GluA4. (b) FN1040 showed significant inhibition of the closed-channel state of GluA1 and GluA2 AMPA receptors, both the GluK1 closed- and open-channel states, but not GluK2. For NMDA type glutamate channels, FN1040 inhibited both the closed- and the open-channel states of GluN1a/2A and GluN1a/2B. One-sample two-tailed Student's t-tests were performed on each column with H$_0$: µ=µ$_0$=1, 1 being the theoretical value of no inhibition (p≤0.5). The significance of the Student's t-test for each column was labeled as the double asterisk (p≤0.1) or the single asterisk (p≤0.5). A one-way ANOVA analysis combing with post hoc Tukey's test indicated that, on the closed-channel conformation, the mean A/A(I) value difference was significant (p≤0.5) only between GluA2 and GluA3, or between GluA2 and GluA4.

We also characterized the potency of FN1040s with a panel of subunits (homomeric channels) and channel types of glutamate ion channel receptors. Such data reflected the preference of inhibition or the subunit selectivity of an aptamer (FIG. 5a). By using the same concentration and measuring A/A(I) value for each of the receptors, we found that FN1040s was selective towards GluA1 and GluA2Q$_{flip}$ AMPA receptor channels (see one-way ANOVA analysis followed by post hoc Tuckey's test to examine the p values for every group pair comparison in the Description of FIGS. 5a and 5b). Furthermore, FN1040s, just like the full-length FN1040, generally exhibited the ability of blocking the closed-channel, but not the open-channel conformation of these channels. FN1040s also showed weaker inhibitory activity on some of the other glutamate receptor subunits such as GluK1 kainate receptor and NMDA receptor channels (i.e., GluN1a/2A, and GluN1a/2B, the two dominant NMDA receptor channel types found in vivo)[39] (see statistical analysis in the Description of FIGS. 5a and 5b).

Figure 5B:
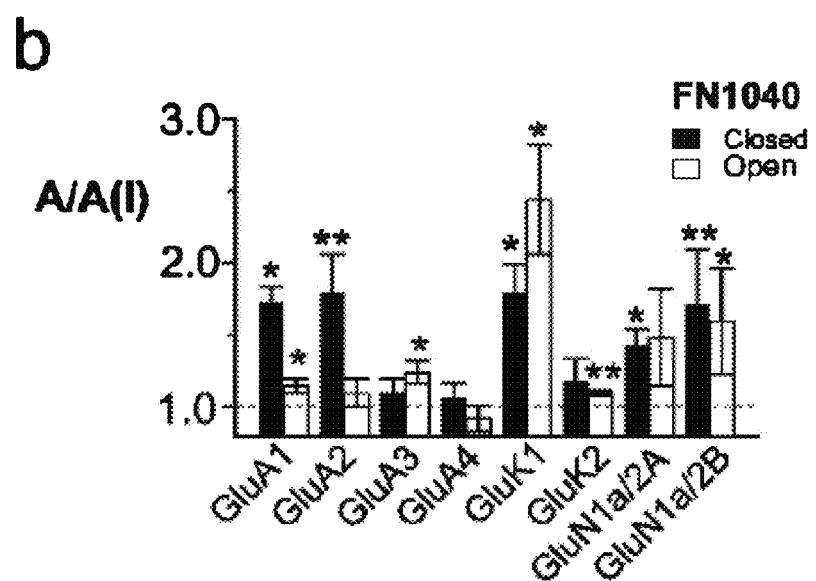
Figure 6:
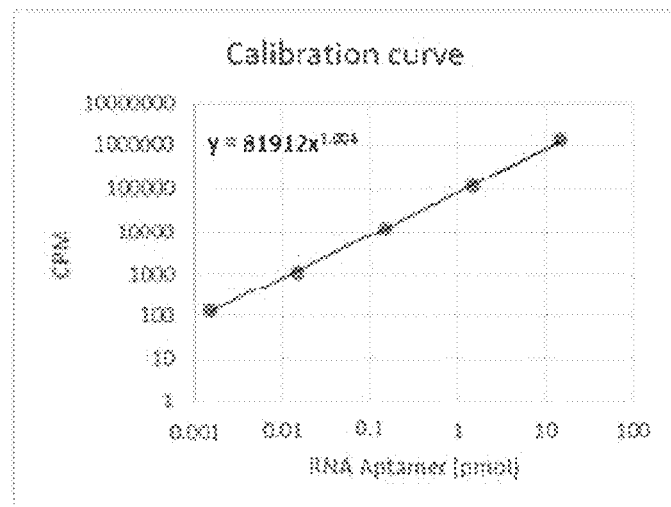
FIG. 6 shows FN1040 distribution throughout CNS including the spinal cord after intracerebroventricular (i.c.v.) infusion. Counts associated with each section are shown in a table (middle panel) with the results shown graphically in the lower panel. Upper panel shows a calibration curve.
Figure 6:
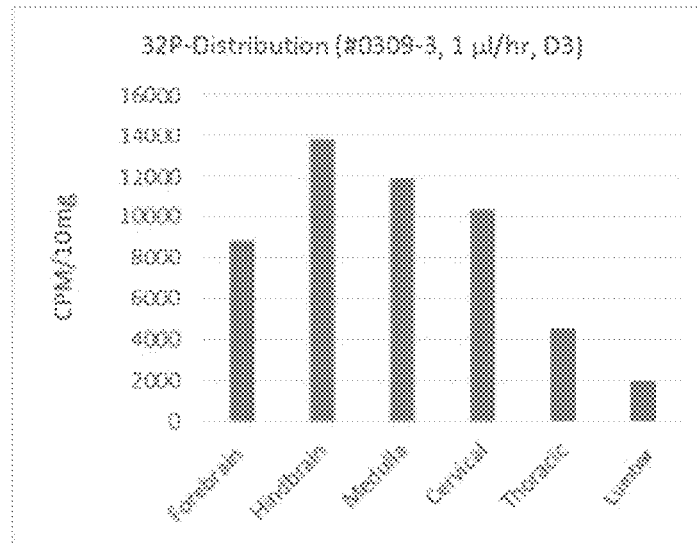

To compare with the selectivity profile of FN1040s with its predecessor, full-length FN1040 aptamer, we also performed a similar selectivity assay for FN1040 (FIG. 5b). As shown, full-length aptamer FN1040 showed, similar to FN1040s, a preference of inhibition of GluA1 and GluA2Q$_{flip}$. Unlike its short version, FN1040 strongly inhibited both kainate and NMDA receptors. Specifically, on kainate receptors, FN1040 showed a stronger inhibition of GluK1 but not GluK2. In addition, FN1040 seemed to block the open-channel conformation of GluK1 effectively if not even more effectively, as compared with the closed-channel conformation. On NMDA receptors, FN1040 inhibited GluN1a/2A, and GluN1a/2B (FIG. 5b). The subunit selectivity assays have shown that the full-length FN1040 aptamer was an antagonist capable of blocking all three subtypes of glutamate receptors, whereas the minimized FN1040s aptamer was selective towards the GluA1 and GluA2 AMPA receptor subunits.

Transcription and Purification of 2'-Fluoro Modified RNAs.

The 2'-fluoro modified RNAs were transcribed at 37° C. overnight by using a T7 RNA polymerase mutant, Y639F/

H784A.[28, 48] The transcription mixture of 30 μl contained 1 μg of DNA template, 200 mM HEPES, 40 mM DTT, 2 mM spermidine, 25 mM MgCl$_2$, 1.5 mM MnCl$_2$, 10% PEG8K, 0.01% Triton X100, 6.7 mM of GTP, 6.7 mM of 2'-F-ATP, 6.7 mM of 2'-F-CTP, 6.7 mM of 2'-F-UTP, 0.02 unit/μl of yeast inorganic pyrophosphatase, and 2.5 μM of Y639F/H784A T7 RNA polymerase. The RNA was purified by using 25 mM HEPES buffer (pH 7.5) in a cylindrical PAGE column.[49]

Receptor Expression and In Vitro Selection.

GluA2Q$_{flip}$ homomeric channels were transiently expressed in HEK-293S cells for SELEX. The transfected cells were harvested 48 hours after transfection. The membrane fragment containing the GluA2Q$_{flip}$ receptor was prepared and quantified as described.[10] The final concentration of membrane-bound receptor in the binding mix was 8 nM, as determined by [$^3$H]AMPA binding. The preparation of the RNA library and the protocol of running the in vitro evolution selection were described previously.[10] For binding in the initial round of selection, the RNA library with ~10$^{14}$ random sequences was dissolved in the extracellular buffer, which contained (in mM) 150 NaCl, 3 KCl, 1 CaCl$_2$, 1 MgCl$_2$, 10 HEPES (pH 7.4). The mixture of the RNA library and the receptor was incubated at 22° C. for 50 min for RNA binding to the receptor in the presence of 0.3 units/μl RNase inhibitor. For elution, a mixture of 250 μM (final concentration) of NBQX and 250 μM of BDZ-f was used. The eluted RNAs were then subject to reverse transcription/PCR to produce new DNA library pool. At the end of the 12th selection round, the DNA pools from rounds 10 to 12 were separately cloned into the pGEM-T easy vector (Invitrogen) for sequencing. By sequence comparison, the enriched sequences were identified and presented in Table 1.

Whole-Cell Current Recording.

Each of the receptors used in this study was transiently expressed in HEK-293S cell.[50] The procedure for whole-cell current recording to assay the inhibitory property of an RNA aptamer was described previously[10]. The electrode for whole-cell recording had a resistance of ~3 MΩ, when filled with the electrode solution (in mM): 110 CsF, 30 CsCl, 4 NaCl, 0.5 CaCl$_2$, 5 EGTA, and 10 HEPES (pH 7.4 adjusted by CsOH). For recording of the NMDA channels, the intracellular solution contained (in mM) 140 CsCl, 1 MgCl$_2$, 0.1 EGTA, and 10 HEPES (pH 7.2 adjusted by Mg(OH)$_2$) and the extracellular solution contained 2 μM of glycine and (in mM) 135 NaCl, 5.4 KCl, 1.8 CaCl$_2$, 10 glucose and 5 HEPES (pH 7.2 adjusted by NaOH).[10] The glutamate-induced whole-cell current was recorded using an Axopatch-200B amplifier at a cutoff frequency of 2-20 kHz by a built-in, eight-pole Bessel filter and digitized at 5-50 kHz sampling frequency using a Digidata 1322A from Axon Instruments (Molecular Devices, Sunnyvale, Calif.). The pClamp 8 software (Molecular Devices) was used for data acquisition. All whole-cell recordings were at −60 mV and 22° C.

Data Analysis of Whole-Cell Current Amplitude.

Whole-cell current amplitude in the absence and presence of an aptamer, A/A(I), as a function of aptamer concentration was used to determine an apparent inhibition constant ($K_{I,app}$), using eq 1.[51] Eq 1 was derived based on the assumption by which an inhibitor binds to one site on the receptor. $\overline{(AL_2)}$ represents the open-channel conformation with n=2 (note that n=2 is just an example to show the $K_{I,\ app}$ can depend on ligand concentration—see below). I is the concentration of the inhibitor, whereas L is the ligand concentration. Φ represents the channel opening equilibrium constant.

$$\frac{A}{A(I)} = 1 + I \frac{\overline{(AL_2)}}{K_{I,app}} \quad \text{eq. 1}$$

$$\overline{(AL_2)} = \frac{\overline{AL_2}}{A + AL + AL_2 + \overline{AL_2}} = \frac{L^2}{L^2(1+\Phi) + 2K_1 L\Phi + K_1^2 \Phi}$$

When glutamate was at a low concentration (L<<K$_1$), most of the receptors in the population were in the closed-channel conformation. Under this condition, the K$_I$ we determined using eq 1 reflected the one for the closed-channel conformation. Likewise, when the glutamate concentration was at a saturation level (L>>K$_1$), the majority of the receptors were in the open-channel conformation. Thus the K$_I$ was related to the open-channel form. Based on this rationale, we used the two ligand concentrations which corresponded to ~4% and ~96% fractions of the open-channel form in order to measure the inhibition constant for the closed- and open-channel conformations[51] of a receptor or channel form.

RNA 5'-end Labeling with $^{32}$P.

The 5'-end phosphate group was removed by incubating with 0.1 unit of calf intestinal phosphatase (New England Biolabs) in a mixture containing 50 mM Tris-HCl (pH 8.5), 0.1 mM EDTA, and 10 pmol RNA. The RNA sample was then purified by phenol/chloroform extraction and ethanol precipitation. The air-dried pellet was dissolved in H$_2$O. Up to 100 pmol of RNA was combined with 25 pmol of [γ-$^{32}$P]ATP (6000 Ci/mmol, 150 mCi/ml, PerkinElmer) and 10 unit of T4 polynucleotide kinase in kinase buffer (50 mM Tris, pH 7.5, 10 mM MgCl$_2$, 5 mM DTT) to a final volume of 20 μl. After an one hour incubation at 37° C., the labeled RNA was purified by NucAway spin columns (Thermo Fisher Scientific).

Homologous Competitive Binding Assay.

FN1040 was transcribed in a transcription reaction mixture with additional 0.4 μM of $^{32}$P-α-ATP (800 Ci/mmol). The $^{32}$P-FN1040 product was separated by 8M urea PAGE and recovered by electroelution method (Elutrap, GE Health). Before mixing with the cell membrane fragments, the RNA was run through a refolding procedure, i.e. 95° C./3'→50° C./30'→room temperature/30'. The binding mixture contained 0.6 nM of GluA2Q$_{flip}$ receptor, 10 ng/μl of yeast tRNA, 10 nM of $^{32}$P-FN1040, and 0 to 1.5 μM of unlabeled FN1040 in the extracelluar buffer. The binding mixture was kept at room temperature for 2 hours and then moved to 4° C. for overnight incubation. After binding, the receptor and the bound hot material were separated from the unbound material by spinning through an extracelluar buffer pre-soaked nylon filter (VWR, 0.45 μm pore size).[37] The filter was washed twice with extracellular buffer. The radio-activity remaining on the filter was counted in a scintillation counter (Beckman LS6500). The binding signal (Y) was plotted against the concentration of the RNA aptamer. Assuming a one-site binding model, we determined the K$_d$ of the aptamer bound to the receptor by fitting the binding data to eq 2[52] below, $$Y = \frac{B_{max} \times [\text{Hot}]}{[\text{Hot}] + [\text{Cold}] + K_d} + NSB \quad \text{eq. 2}$$

where Y represents the total binding in the presence of various concentration of cold FN1040, B$_{max}$ is the maximum possible binding sites, [Hot] and [Cold] are the unbound hot FN1040 and cold FN1040 concentrations, and NSB is the non-specific binding.

RNA Stability Assay.

An RNA sample (2 µg) prepared in 20 µl of 1× extracellular buffer was mixed with either 20 µl of HEK-293 cell culture medium containing 10% FBS or 20 µl of rat CSF (rat CSF was provided by Professor Jacqueline Sagen at the University of Miami). The mixture was sealed and kept at 37° C. for up to one week. Samples were drawn every day from the mixture and mixed with equal volume of the loading dye, which contained 99% formamide and 0.03% bromophenol blue. The digestion pattern of the RNA was examined on a denatured 10% PAGE with ethidium bromide staining. The gel was digitized, and the relative intensities of the bands were estimated.

Statistical Data Analysis.

Unless noted otherwise, each data point, such as A/A(I) or binding data point, was an average of at least three measurements (each of the whole-cell recording data was collected from at least three cells). Uncertainties reported refer to standard deviation from the mean. Student's t-test, ANOVA and post hoc Tuckey's test were performed by using software package R-Studio (version 1.0.136).[53, 54] See additional details in the brief description of FIG. 5.

Aptamers in ALS Mouse Model

Figure 11:
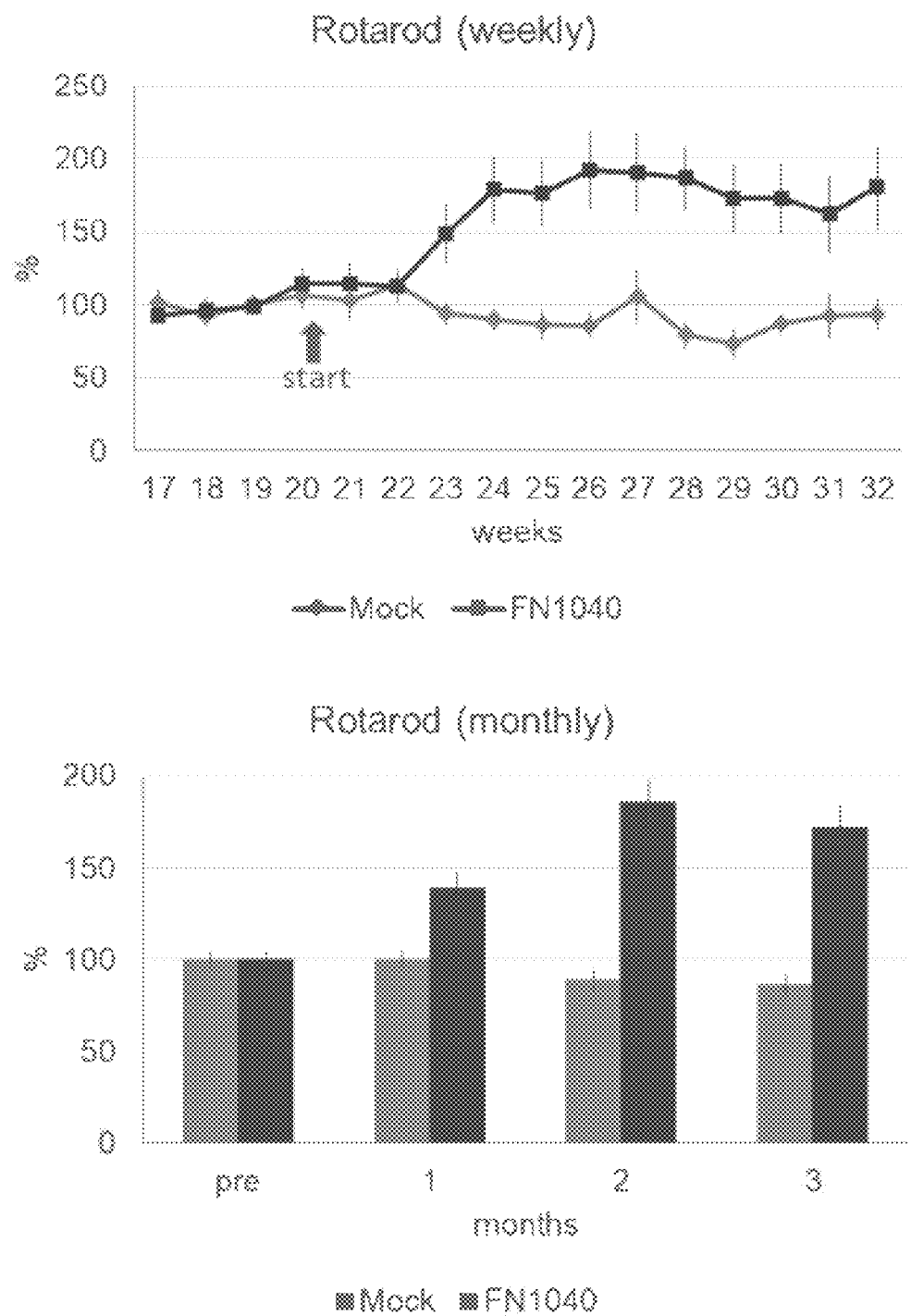
FIG. 11 FN1040 30 µM to AR2 mice (n≤14 for each time point). Each mouse was infused with 0.5 µl/h aptamer by using an Alzet pump. Aptamer treatment started at week 20 (green arrow), and the study is on-going. As seen, FN1040-treated AR2 mice have shown a significant improvement in their motor function, measured by rotarod performance, as compared with vehicle-untreated or mock group. In fact, aptamer treated mice performed even better on rotarod than 20 mg/kg/day of perampanel administration (Akamatsu et al. 2016. Sci Report 6:28649|DOI: 10.1038/srep28649).

In one embodiment, administration of 30 µM FN1040 to mice in an ALS mouse model improved the mice's performance in a rotarod performance test. Results are shown in FIG. 11.

Aptamers (FN1040 and FN1008) were tested in the AR2 ALS mouse model. The AR2 mouse is a conditional ADAR2 knockout, created in the laboratory of S. Kwak (see Hideyama et al. *Induced loss of ADAR2 engenders slow death of motor neurons from Q/R site-unedited GluR2. J Neurosci* 30, 11917-11925).

ADAR2 catalyzes the conversion of adenosine to inosine at the pre-mRNA level for the Q/R editing site on GluA2. Expression of Q/R site-unedited GluA2 or GluA2Q, due to Q/R editing defect, as is found in sporadic ALS patients, causes motor neuron death presumably via the $Ca^{2+}$-permeable AMPA receptor-mediated excitotoxicity.

In healthy controls, all GluA2 AMPA receptor subunits are in the Q/R edited form or the R form. The GluA2R forms channels with other subunits that are not Ca2+-permeable.

These AR mice show a decline in motor function commensurate with the slow death of ADAR2-deficient motor neurons in the spinal cord and cranial motor nerve nuclei. The AR2 mouse most closely models sporadic ALS by the following evidence. (i) The majority of the motor neurons in sporadic ALS exhibit both ADAR2 downregulation and TDP-43 mislocation. In other words, AR2 mice exhibit TDP-43 mislocalization in the ADAR2-lacking motor neurons, indicating a correlation or a common pathogenic mechanism. (ii) In a considerable proportion of spinal cord motor neurons of the majority of the sporadic ALS patients, TDP-43 is absent from the nucleus in which it normally resides but is now localized abnormally in cytoplasmic inclusions. (iii) Abnormal expression and activity of $Ca^{2+}$-permeable AMPA receptors activates calpain, a $Ca^{2+}$-dependent cysteine protease, which generates carboxy-terminal-cleaved TDP-43 fragments and causes TDP-43 mislocalization in the motor neurons. The use of AR2 mouse model will thus allow us to not only block the excessive AMPA receptor activity in this system but also potentially inhibit TDP-43 pathology.

Aptamers as Anti-Nociceptive

One embodiment disclosed herein has the ability to reduce pain. To test aptamers for potential analgesic effects, a clip compression injury-induced pain model was used. Aptamer FN1008 was tested using this model. A total of 8 animals with spinal cord injury (SCI) were tested for 3-4 weeks to be sure they developed chronic SCI pain symptoms before injection of the aptamer; the animals then received repeated intrathecal injections and testing of the aptamer (n=5) or control (n=3).

Figure 12:
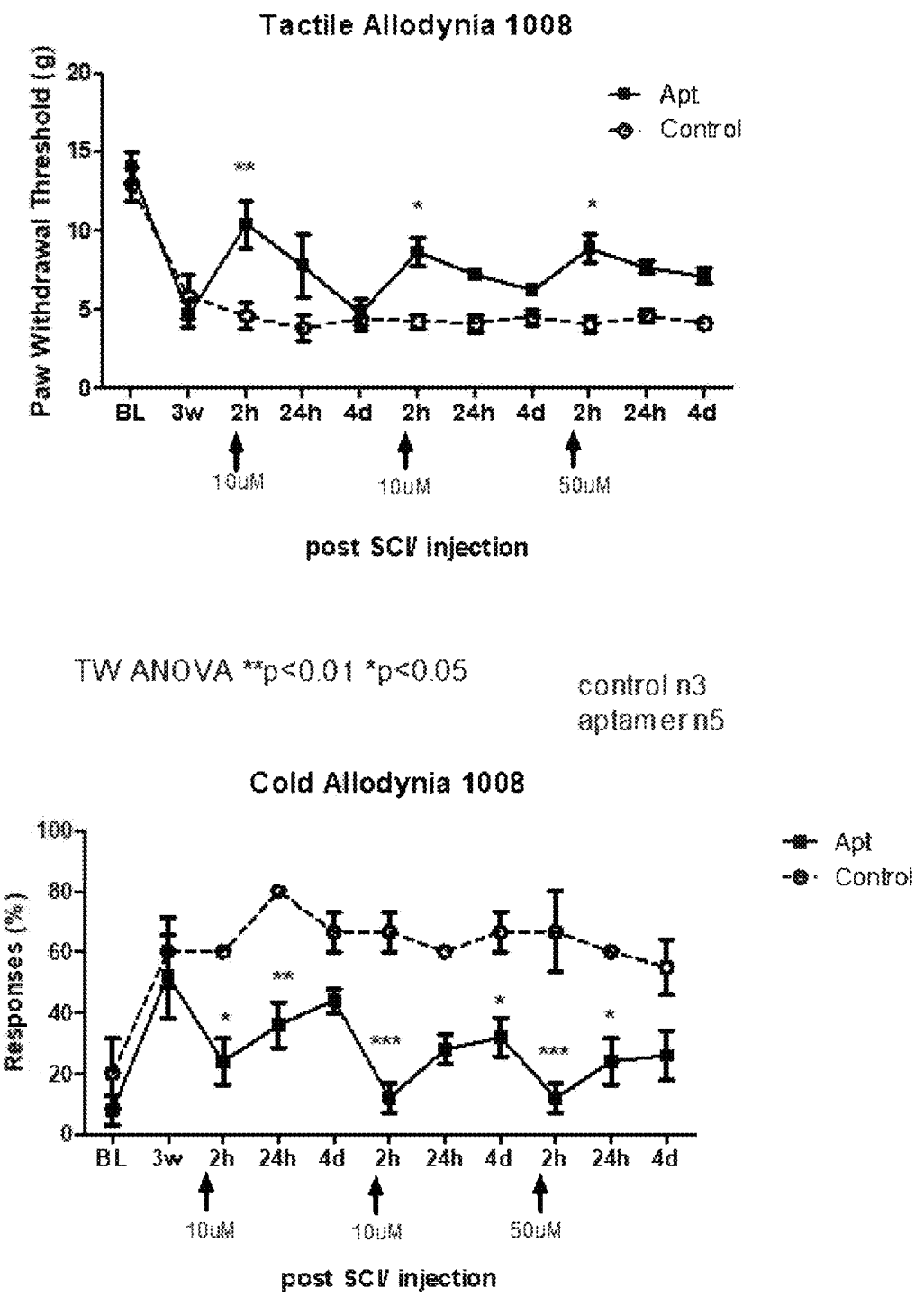
FIG. 12 shows the anti-nociceptive effect of an aptamer of the disclosure. FN1008 aptamer was injected intrathecally post spinal cord injury (SCI) induced by clip compression, and tests for tactile (top panel) and cold (lower panel) allodynia were measured (described in Aptamers as Anti-nociceptive). Responses were determined before SCI at baseline (BL), indicated in the x-axis, at 3 weeks following SCI when pain symptoms were established, and at several intervals following the intrathecal injection of aptamer or vehicle (2 hr, 24 hr, 4 days). To determine whether anti-nociceptive effects could be repeatedly elicited, we administered the 2nd and 3rd bolus injection of the aptamer, following the test on the 4th day of each series (at arrows); this anti-nociceptive testing schedule was repeated thereafter. Since this was a pilot dosing study, the third injection tested a higher aptamer dose. No untoward side effects were observed. The behavioral testing was done as indicated in the plot. Before i.t. injection, a PAGE was run to check for possible absorption of aptamer in the catheter. No significant reduction of RNA in the samples that passed through the catheter was found.

FN1008 aptamer was injected intrathecally post spinal injury induced by clip compression, and tests for tactile (FIG. 12, top panel) and cold (lower panel) allodynia were measured (described in the description of FIG. 12). Responses were determined before SCI (at baseline, BL, indicated in the x-axis), at 3 weeks following SCI when pain symptoms were established, and at several intervals following the intrathecal injection of aptamer or vehicle (2 hr, 24 hr, 4 days). To determine whether antinociceptive effects could be repeatedly elicited, we administered 2nd and 3rd bolus injection of the aptamer, following the test on the 4th day of each series (at arrows); this antinociceptive testing schedule was repeated thereafter. Since this was a pilot dosing study, the third injection tested a higher aptamer dose. No untoward side effects were observed (see text for details). The behavioral testing was done as indicated in the plot. Before i.t. injection, a PAGE was run to check for possible absorption of aptamer in the catheter. We found no significant reduction of RNA in the samples that passed through the catheter.

As shown in FIG. 12, the intrathecal injection of FN1008 aptamer reduced both tactile and cold allodynia as measured at 2 hr post-injection. These acute anti-allodynic effects could be repeatedly elicited with repeated aptamer dosing (at arrows). The aptamer effects were particularly robust in reducing cold hypersensitivity, which was nearly completely eliminated following the 2nd and 3rd injections. In addition, effects on cold allodynia were prolonged for an additional 24 hrs and possibly up to 4 days in some cases. It should be noted that potential untoward side effects, such as piloerection, sedation, agitation, porphyria, and motor reflexes (righting, placing), were monitored. Yet no adverse physiological or reflex side effects have been observed thus far, even after a higher dose was administered (i.e., the 3rd injection). These results suggest a strong and a lasting effect of FN1008, particularly in reducing cold allodynia, as well as partial reduction of tactile allodynia, compared with vehicle. Another aptamer, FN1040, was also tested but found to be less effective under the same experimental condition.

REFERENCES

[1] Traynelis, S. F., Wollmuth, L. P., McBain, C. J., Menniti, F. S., Vance, K. M., Ogden, K. K., Hansen, K. B., Yuan, H., Myers, S. J., and Dingledine, R. (2010) Glutamate receptor ion channels: structure, regulation, and function, *Pharmacol Rev* 62, 405-496.

[2] Kawahara, Y., Ito, K., Sun, H., Aizawa, H., Kanazawa, I., and Kwak, S. (2004) Glutamate receptors: RNA editing and death of motor neurons, *Nature* 427, 801.

[3] Waterhouse, R. N. (2003) Determination of lipophilicity and its use as a predictor of blood-brain barrier penetration of molecular imaging agents, *Molecular imaging and biology: MIB: the official publication of the Academy of Molecular Imaging* 5, 376-389.

[4] Weiser, T. (2005) AMPA receptor antagonists for the treatment of stroke, *Current drug targets. CNS and neurological disorders* 4, 153-159.

[5] Lipton, S. A. (2006) Paradigm shift in neuroprotection by NMDA receptor blockade: memantine and beyond, *Nature reviews. Drug discovery* 5, 160-170.

[6] Rogawski, M. A. (2000) Low affinity channel blocking (uncompetitive) NMDA receptor antagonists as therapeutic agents—toward an understanding of their favorable tolerability, *Amino Acids* 19, 133-149.

[7] Vemula, V., Lagishetty, V., and Lingala, S. (2010) Solubility enhancement techniques, *International journal of pharmaceutical sciences review and research* 5, 41-51.

[8] Park, J. S., Wang, C., Han, Y., Huang, Z., and Niu, L. (2011) Potent and selective inhibition of a single alpha-amino-3-hydroxy-5-methyl-4-isoxazolepropionic acid (AMPA) receptor subunit by an RNA aptamer, *The Journal of biological chemistry* 286, 15608-15617.

[9] Huang, Z., Han, Y., Wang, C., and Niu, L. (2010) Potent and selective inhibition of the open-channel conformation of AMPA receptors by an RNA aptamer, *Biochemistry* 49, 5790-5798.

[10] Huang, Z., Pei, W., Jayaseelan, S., Shi, H., and Niu, L. (2007) RNA aptamers selected against the GluR2 glutamate receptor channel, *Biochemistry* 46, 12648-12655.

[11] Lee, G., MacLean, D. M., Ulrich, H., Zhao, X., Aronowski, J., and Jayaraman, V. (2014) RNA based antagonist of NMDA receptors, *ACS Chem Neurosci* 5, 559-567.

[12] Du, M., Ulrich, H., Zhao, X., Aronowski, J., and Jayaraman, V. (2007) Water soluble RNA based antagonist of AMPA receptors, *Neuropharmacology* 53, 242-251.

[13] Schieven, G. L., Blank, A., and Dekker, C. A. (1982) Ribonucleases of human cerebrospinal fluid: detection of altered glycosylation relative to their serum counterparts, *Biochemistry* 21, 5148-5155.

[14] Zhou, J., and Rossi, J. (2017) Aptamers as targeted therapeutics: current potential and challenges, *Nat Rev Drug Discov* 16, 181-202.

[15] Sundaram, P., Kurniawan, H., Byrne, M. E., and Wower, J. (2013) Therapeutic RNA aptamers in clinical trials, *Eur J Pharm Sci* 48, 259-271.

[16] Shigdar, S., Macdonald, J., O'Connor, M., Wang, T., Xiang, D., Al Shamaileh, H., Qiao, L., Wei, M., Zhou, S. F., Zhu, Y., Kong, L., Bhattacharya, S., Li, C., and Duan, W. (2013) Aptamers as theranostic agents: modifications, serum stability and functionalisation, *Sensors (Basel)* 13, 13624-13637.

[17] Brody, E. N., and Gold, L. (2000) Aptamers as therapeutic and diagnostic agents, *Reviews in Molecular Biotechnology (share volume with J of biotechnology)* 74, 5-13.

[18] Sabahi, A., Guidry, J., Inamati, G. B., Manoharan, M., and Wittung-Stafshede, P. (2001) Hybridization of 2'-ribose modified mixed-sequence oligonucleotides: thermodynamic and kinetic studies, *Nucleic Acids Res* 29, 2163-2170.

[19] Pallan, P. S., Prakash, T. P., de Leon, A. R., and Egli, M. (2016) Limits of RNA 2'-OH Mimicry by Fluorine: Crystal Structure of Bacillus halodurans RNase H Bound to a 2'-FRNA:DNA Hybrid, *Biochemistry* 55, 5321-5325.

[20] Anosova, I., Kowal, E. A., Dunn, M. R., Chaput, J. C., Van Horn, W. D., and Egli, M. (2016) The structural diversity of artificial genetic polymers, *Nucleic Acids Res* 44, 1007-1021.

[21] Lorsch, J. R., and Szostak, J. W. (1994) In vitro evolution of new ribozymes with polynucleotide kinase activity, *Nature* 371, 31-36.

[22] Cazenave, C., and Uhlenbeck, O. C. (1994) RNA template-directed RNA synthesis by T7 RNA polymerase, *Proc Natl Acad Sci USA* 91, 6972-6976.

[23] Milligan, J. F., Groebe, D. R., Witherell, G. W., and Uhlenbeck, O. C. (1987) Oligoribonucleotide synthesis using T7 RNA polymerase and synthetic DNA templates, *Nucleic acids research* 15, 8783-8798.

[24] Burmeister, P. E., Lewis, S. D., Silva, R. F., Preiss, J. R., Horwitz, L. R., Pendergrast, P. S., McCauley, T. G., Kurz, J. C., Epstein, D. M., Wilson, C., and Keefe, A. D. (2005) Direct in vitro selection of a 2'-O-methyl aptamer to VEGF, *Chem Biol* 12, 25-33.

[25] Brieba, L. G., and Sousa, R. (2000) Roles of histidine 784 and tyrosine 639 in ribose discrimination by T7 RNA polymerase, *Biochemistry* 39, 919-923.

[26] Chelliserrykattil, J., and Ellington, A. D. (2004) Evolution of a T7 RNA polymerase variant that transcribes 2'-O-methyl RNA, *Nat Biotechnol* 22, 1155-1160.

[27] Adler, A., Forster, N., Homann, M., and Goringer, H. U. (2008) Post-SELEX chemical optimization of a trypanosome-specific RNA aptamer, *Comb Chem High Throughput Screen* 11, 16-23.

[28] Padilla, R., and Sousa, R. (1999) Efficient synthesis of nucleic acids heavily modified with non-canonical ribose 2'-groups using a mutantT7 RNA polymerase (RNAP), *Nucleic Acids Res* 27, 1561-1563.

[29] Honore, T., Davies, S. N., Drejer, J., Fletcher, E. J., Jacobsen, P., Lodge, D., and Nielsen, F. E. (1988) Quinoxalinediones: potent competitive non-NMDA glutamate receptor antagonists, *Science* 241, 701-703.

[30] Wang, C., Han, Y., Wu, A., Solyom, S., and Niu, L. (2014) Mechanism and site of inhibition of AMPA receptors: pairing a thiadiazole with a 2,3-benzodiazepine scaffold, *ACS Chem Neurosci* 5, 138-147.

[31] Jin, R., Horning, M., Mayer, M. L., and Gouaux, E. (2002) Mechanism of activation and selectivity in a ligand-gated ion channel: structural and functional studies of GluR2 and quisqualate, *Biochemistry* 41, 15635-15643.

[32] Li, G., Pei, W., and Niu, L. (2003) Channel-opening kinetics of GluR2Q(flip) AMPA receptor: a laser-pulse photolysis study, *Biochemistry* 42, 12358-12366.

[33] Wimberly, B. T., Guymon, R., McCutcheon, J. P., White, S. W., and Ramakrishnan, V. (1999) A detailed view of a ribosomal active site: the structure of the L11-RNA complex, *Cell* 97, 491-502.

[34] Biou, V., Yaremchuk, A., Tukalo, M., and Cusack, S. (1994) The 2.9 A crystal structure of *T. thermophilus* seryl-tRNA synthetase complexed with tRNA(Ser), *Science* 263, 1404-1410.

[35] Zuker, M. (2003) Mfold web server for nucleic acid folding and hybridization prediction, *Nucleic Acids Res* 31, 3406-3415.

[36] Patra, A., Paolillo, M., Charisse, K., Manoharan, M., Rozners, E., and Egli, M. (2012) 2'-Fluoro RNA shows increased Watson-Crick H-bonding strength and stacking relative to RNA: evidence from NMR and thermodynamic data, *Angewandte Chemie* 51, 11863-11866.

[37] Jaremko, W. J., Huang, Z., Wen, W., Wu, A., Karl, N., and Niu, L. (2017) Identification and characterization of RNA aptamers: A long aptamer blocks the AMPA receptor and a short aptamer blocks both AMPA and kainate receptors, *The Journal of biological chemistry* 292, 7338-7347.

[38] Huang, Z., Pei, W., Han, Y., Jayaseelan, S., Shekhtman, A., Shi, H., and Niu, L. (2009) One RNA aptamer sequence, two structures: a collaborating pair that inhibits AMPA receptors, *Nucleic Acids Res* 37, 4022-4032.
[39] Dingledine, R., Borges, K., Bowie, D., and Traynelis, S. F. (1999) The glutamate receptor ion channels, *Pharmacol Rev* 51, 7-61.
[40] Ruckman, J., Green, L. S., Beeson, J., Waugh, S., Gillette, W. L., Henninger, D. D., Claesson-Welsh, L., and Janjic, N. (1998) 2'-Fluoropyrimidine RNA-based aptamers to the 165-amino acid form of vascular endothelial growth factor (VEGF165). Inhibition of receptor binding and VEGF-induced vascular permeability through interactions requiring the exon 7-encoded domain, *The Journal of biological chemistry* 273, 20556-20567.
[41] Bell, C., Lynam, E., Landfair, D. J., Janjic, N., and Wiles, M. E. (1999) Oligonucleotide NX1838 inhibits VEGF165-mediated cellular responses in vitro, *In Vitro Cell Dev Biol Anim* 35, 533-542.
[42] Tucker, C. E., Chen, L. S., Judkins, M. B., Farmer, J. A., Gill, S. C., and Drolet, D. W. (1999) Detection and plasma pharmacokinetics of an anti-vascular endothelial growth factor oligonucleotide-aptamer (NX1838) in rhesus monkeys, *J Chromatogr B Biomed Sci Appl* 732, 203-212.
[43] Beneyto, M., and Meador-Woodruff, J. H. (2004) Expression of transcripts encoding AMPA receptor subunits and associated postsynaptic proteins in the macaque brain, *J Comp Neurol* 468, 530-554.
[44] Keinanen, K., Wisden, W., Sommer, B., Werner, P., Herb, A., Verdoorn, T. A., Sakmann, B., and Seeburg, P. H. (1990) A family of AMPA-selective glutamate receptors, *Science*. 249, 556-560.
[45] Petrenko, A. B., Yamakura, T., Baba, H., and Shimoji, K. (2003) The role of N-methyl-D-aspartate (NMDA) receptors in pain: a review, *Anesth Analg* 97, 1108-1116.
[46] Chappell, A. S., Iyengar, S., Lobo, E. D., and Prucka, W. R. (2014) Results from clinical trials of a selective ionotropic glutamate receptor 5 (iGluR5) antagonist, LY5454694 tosylate, in 2 chronic pain conditions, *Pain* 155, 1140-1149.
[47] Bliss, T. V., Collingridge, G. L., Kaang, B. K., and Zhuo, M. (2016) Synaptic plasticity in the anterior cingulate cortex in acute and chronic pain, *Nat Rev Neurosci* 17, 485-496.
[48] Padilla, R., and Sousa, R. (2002) A Y639F/H784A T7 RNA polymerase double mutant displays superior properties for synthesizing RNAs with non-canonical NTPs, *Nucleic Acids Res* 30, e138.
[49] Huang, Z., Jayaseelan, S., Hebert, J., Seo, H., and Niu, L. (2013) Single-nucleotide resolution of RNAs up to 59 nucleotides by high-performance liquid chromatography, *Analytical biochemistry* 435, 35-43.
[50] Huang, Z., Li, G., Pei, W., Sosa, L. A., and Niu, L. (2005) Enhancing protein expression in single HEK 293 cells, *J Neurosci Methods* 142, 159-166.
[51] Li, G., and Niu, L. (2004) How fast does the GluR1Qflip channel open?, *The Journal of biological chemistry* 279, 3990-3997.
[52] Swillens, S. (1995) Interpretation of binding curves obtained with high receptor concentrations: practical aid for computer analysis, *Mol Pharmacol* 47, 1197-1203.
[53] Team, R. (2015) RStudio: Integrated Development for R, 1.0.136 ed., RStudio Inc.
[54] Team, R. C. (2013) R: A language and environment for statistical computing, R Foundation for Statistical Computing, Vienna, Austria.
[55] Hama, A., and Sagen, J. (2007) Behavioral characterization and effect of clinical drugs in a rat model of pain following spinal cord compression. *Brain Res* 1185, 117-128
[56] Chiou-Tan, F. Y., Tuel, S. M., Johnson, J. C., Priebe, M. M., Hirsh, D. D., and Strayer, J. R. (1996) Effect of mexiletine on spinal cord injury dysesthetic pain. *Am J Phys Med Rehabil* 75, 84-87
[57] Xu, X. J., Hao, J. X., Aldskogius, H., Seiger, A., and Wiesenfeld-Hallin, Z. (1992) Chronic pain-related syndrome in rats after ischemic spinal cord lesion: a possible animal model for pain in patients with spinal cord injury. *Pain* 48, 279-290
[58] Bruce, J. C., Oatway, M. A., and Weaver, L. C. (2002) Chronic pain after clip-compression injury of the rat spinal cord. *Exp Neurol* 178, 33-48
[59] Hideyama, T., Yamashita, T., Suzuki, T., Tsuji, S., Higuchi, M., Seeburg, P. H., Takahashi, R., Misawa, H., and Kwak, S. (2010) Induced loss of ADAR2 engenders slow death of motor neurons from Q/R site-unedited GluR2. *J Neurosci* 30, 11917-11925

The invention claimed is:

1. A synthetic RNA oligonucleotide consisting of a nucleotide sequence selected from the group consisting of SEQ ID NO: 1, SEQ ID NO: 2 and SEQ ID NO: 11, wherein A, C, and U triphosphates (ATPs, CTPs and UTPs) of said oligonucleotide are 2'-fluoro-modified.

2. A synthetic RNA oligonucleotide comprising a nucleotide sequence selected from the group consisting of SEQ ID NO: 1, SEQ ID NO: 2, and SEQ ID NO: 11, wherein A, C, and U triphosphates (ATPs, CTPs and UTPs) of said oligonucleotide are 2'-fluoro-modified.

3. The synthetic RNA oligonucleotide of claim 1, wherein said oligonucleotide is ribonuclease resistant.

4. The synthetic RNA oligonucleotide of claim 2, wherein said oligonucleotide is ribonuclease resistant.

5. A pharmaceutical composition comprising the synthetic RNA oligonucleotide of claim 1.

6. The pharmaceutical composition of claim 5, further comprising a pharmaceutically acceptable carrier.

7. A pharmaceutical composition comprising the synthetic RNA oligonucleotide of claim 2.

8. The pharmaceutical composition of claim 7, further comprising a pharmaceutically acceptable carrier.

9. A method for reducing neuropathic pain in a mammal comprising administering a therapeutically effective amount of a synthetic RNA oligonucleotide of claim 1.

10. A method for reducing neuropathic pain in a mammal comprising administering a therapeutically effective amount of a synthetic RNA oligonucleotide of claim 2.

11. A method for reducing neuropathic pain in a mammal comprising administering a therapeutically effective amount of a pharmaceutical composition of claim 5.

12. A method for reducing neuropathic pain in a mammal comprising administering a therapeutically effective amount of a pharmaceutical composition of claim 6.

13. A method for reducing neuropathic pain in a mammal comprising administering a therapeutically effective amount of a pharmaceutical composition of claim 7.

14. A method for reducing neuropathic pain in a mammal comprising administering a therapeutically effective amount of a pharmaceutical composition of claim 8.

15. A method for treating neurological diseases and disorders selected from the group consisting of epilepsy and amyotrophic lateral sclerosis comprising administering to a mammal a therapeutically effective amount of a synthetic RNA oligonucleotide of claim 1.

16. A method for treating neurological diseases and disorders selected from the group consisting of epilepsy and amyotrophic lateral sclerosis comprising administering to a mammal a therapeutically effective amount of a synthetic RNA oligonucleotide of claim 2.

* * * * *